United States Patent
Gokaraju et al.

(10) Patent No.: US 8,551,496 B2
(45) Date of Patent: Oct. 8, 2013

(54) BOSWELLIA LOW POLAR GUM RESIN EXTRACT AND ITS SYNERGISTIC COMPOSITIONS

(75) Inventors: Ganga Raju Gokaraju, Vijayawada (IN); Rama Raju Gokaraju, Vijayawada (IN); Ventaka Kanaka Ranga Raju Gokaraju, Vijayawada (IN); Trimurtulu Golakoti, Vijayawada (IN); Kiran Bhupathiraju, Vijayawada (IN)

(73) Assignee: Laila Nutraceuticals, Vijayawada (IN)

( * ) Notice: Subject to any disclaimer, the term of this patent is extended or adjusted under 35 U.S.C. 154(b) by 0 days.

(21) Appl. No.: 13/584,099

(22) Filed: Aug. 13, 2012

(65) Prior Publication Data

US 2012/0301432 A1 Nov. 29, 2012

Related U.S. Application Data

(63) Continuation-in-part of application No. PCT/IN2010/000233, filed on Apr. 12, 2010.

(30) Foreign Application Priority Data

Feb. 15, 2010 (IN) .............................. 384/CHE/2010

(51) Int. Cl.
*A61K 31/00* (2006.01)
*A61K 35/00* (2006.01)
*A61K 36/00* (2006.01)
*A61K 36/906* (2006.01)

(52) U.S. Cl.
USPC ...................... 424/195.18; 424/725; 424/756

(58) Field of Classification Search
None
See application file for complete search history.

(56) References Cited

U.S. PATENT DOCUMENTS

| | | | |
|---|---|---|---|
| 5,629,351 A * | 5/1997 | Taneja et al. | 514/765 |
| 6,589,516 B1 * | 7/2003 | Eyre et al. | 424/70.1 |
| 2004/0202709 A1 | 10/2004 | Kirby et al. | |
| 2005/0282772 A1 * | 12/2005 | Gokaraju et al. | 514/54 |
| 2006/0040000 A1 | 2/2006 | Gokaraju et al. | |
| 2006/0062859 A1 | 3/2006 | Blum et al. | |
| 2006/0280811 A1 | 12/2006 | Bombardelli | |
| 2007/0281045 A1 | 12/2007 | Tripp et al. | |
| 2008/0275117 A1 | 11/2008 | Li et al. | |
| 2008/0317885 A1 | 12/2008 | Baker | |

FOREIGN PATENT DOCUMENTS

WO 0215916 2/2002

OTHER PUBLICATIONS

Kasali et al. (2002) Flavour Fragr. J. 17: 462-464.*
Krohn et al. (2001) Phytochem. Anal. 12: 374-376.*
Mahajan et al. (1995) Phytochemistry, vol. 39, No. 2, pp. 453-455.*
Ammon (2006) Planta Medical—Natural Products and Medicinal Plant Research 72.12 (2006): 1100-1116.*
Chevrier et al. (2005) Clin. Diagn. Lab. Immunol. 12(5): 575-580.*
Houssen et al. (2010) Clinical Biochemistry 43: 887-890.*
Baser, S. Chemical Investigations on *Boswellia* Species, University of Hamburg (online), Mar. 18, 2005, pp. 1-256, retrieved from the Internet: (http://www.boswellness.com/sites/default/files/pdfs/DissertationBasar.pdf) on Aug. 10, 2012.
Al-Harrasi et al., Phytochemical Analysis of the Essential Oil from Botanically Certified Oleogum Resin of *Boswellia sacra* (Omani Luban), Molecules. Sep. 16, 2008. vol. 13, No. 9, pp. 2181-2189.
Ehrman et al., Phytochemical Databases of Chinese Herbal Constituents and Bioactive Plant Compounds with Known Target Specificities. Journal of Chemical Information and Modelling, Jan. 9, 2007. vol. 47, No. 2, pp. 254-263.
Cuaz-Perolin et al., Antiinflammatory and Antiatherogenic Effects of the NF-kB Inhibitor Acetyl-11-Keto-B-Boswellic Acid in LPS-Challenged ApoE_/_Mice, Arterioscler Thromb Vasc Biol. 2008; 28:272-277.
Kimmatkar et al., Efficacy and tolerability of *Boswellia serrata* extract in treatment of osteoarthritis of knee—A randomized double blind placebo controlled trial. Phytomedicine 10: 3-7 (2003).
Ernst, Frankincense:systematic review, BMJ 2008; 337:a2813.
Safayhi et al., Inhibition by Boswellic Acids of Huma Leukocyte Elastase, Journal of Pharmacology and Experimental Therapeutics 281:460-463. 1997.
Sailer et al., Acetyl-11-keto-B-boswellic acid (AKBA): structure requirements for binding and 5-lipoxygenase inhibitory activity. British Journal of Pharmacology. (1996) 117, 615-618.
International Search Report dated for PCT/IN2010/000233 dated Oct. 5, 2010.

* cited by examiner

*Primary Examiner* — Chris R Tate
*Assistant Examiner* — Russell Fiebig
(74) *Attorney, Agent, or Firm* — Kramer Amado, P.C.

(57) ABSTRACT

The present disclosure describes *Boswellia* low polar gum resin extract (BLPRE) comprising novel phytochemical composition of sesquiterpenes, diterpenes, triterpenes and other phytochemical(s) obtained from gum resin of *Boswellia* species. The present disclosure also describes compositions comprising BLPRE in combination with one or more component(s) selected from biologically active ingredient(s), functional ingredient(s), excipient(s), diluents(s), carrier(s) and additive(s) or mixtures thereof. Further the present disclosure also provides synergistic composition(s) comprising *Boswellia* low polar gum resin extract (BLPRE) and at least one component selected from but not limited to extract(s), fraction(s), phytochemical(s) or their salts or mixtures thereof derived from *Boswellia* species or *Curcuma* species.

28 Claims, 4 Drawing Sheets

A: chromatogram at 252 nm

B: chromatogram at 210 nm

BOSWELLIA LOW POLAR GUM RESIN EXTRACT AND ITS SYNERGISTIC COMPOSITIONS

CROSS-REFERENCE TO APPLICATIONS

This application is a continuation-in-part of international application PCT/IN2010/000233, published as WO 2011/099029, filed on Apr. 12, 2010. The entire disclosures of international application PCT/IN2010/000233 is hereby incorporated by reference in their entirety.

FIELD OF THE DISCLOSURE

The present disclosure provides *Boswellia* low polar gum resin extract (BLPRE) comprising novel phytochemical composition(s) of sesquiterpenes, diterpenes, triterpenes and other phytochemical(s) obtained from gum resin of *Boswellia* species.

The disclosure also provides compositions comprising *Boswellia* low polar gum resin extract (BLPRE) and at least one component selected from biologically active ingredient(s), functional ingredient(s), excipient(s), diluents(s), carrier(s) and additive(s) or mixtures thereof.

Further the disclosure also provides synergistic composition(s) comprising *Boswellia* low polar gum resin extract (BLPRE) and at least one component selected from extract(s), fraction(s), phytochemical(s) and their salts or mixtures thereof derived from *Boswellia* species or *Curcuma* species.

BACKGROUND

There are numerous pharmaceutical, herbal ingredient(s) and biologically active molecules that are effective in vitro for a disease or disorder. However, several of them are not effective or not bioavailable in vivo (warm blooded animals). It is thus important to explore, identify and invent safe and effective compound(s) or composition(s) that helps increase the in vivo activity of such pharmaceutical or herbal ingredient(s) through synergism. In this process the inventors have screened a number of extracts, fractions, phytochemical(s) and compound(s) originating from plants, animals and microorganisms; individually and in combinations.

The gum resin of *Boswellia* has been very widely used since ancient times. For example, the gum resin of *Boswellia serrata* (Burseraceae) plant has long been in use for the treatment of rheumatoid arthritis and gout by the practitioners of Ayurvedic medicines in the Indian system of medicine. Various extracts of the gum resin have shown potent anti-inflammatory and anti-atherogenic activity in laboratory. The extract of *Boswellia* was found to be a potent anti-arthritic. *Boswellia* gum resin and its extracts also demonstrated significant therapeutic improvements in human clinical trials confirming the in vivo anti-inflammatory effects.

The origin of the anti-inflammatory action of *Boswellia* gum resin and its extracts has been attributed to a group of triterpene acids called Boswellic acids that were isolated from the gum resin of *Boswellia serrata*. Boswellic acids exert anti-inflammatory actions by inhibiting 5-lipoxygenase (5-LOX). 5-LOX is a key enzyme for the biosynthesis of leukotrienes from arachidonic acid. Leukotrienes are considered to be involved in the initiation and propagation of a variety of inflammatory diseases. In addition to their 5-lipoxygenase inhibition, Boswellic acids inhibit human leukocyte elastase (HLE), an enzyme of different pro-inflammatory pathway. 3-O-Acetyl-11-keto-β-Boswellic acid (AKBA) is biologically the most active component among its congeners, with an $IC_{50}$ of 1.5 µM for the inhibition of 5-LOX.

There is, however, no known prior art relating to *Boswellia* low polar gum resin extract (BLPRE) comprising a phytochemical composition of sesquiterpenes, diterpenes, and triterpenes or compositions thereof, for the prevention, control and treatment of disorders or diseases in warm blooded animals.

SUMMARY

In an important aspect, the present disclosure provides a *Boswellia* low polar gum resin extract (BLPRE) comprising novel phytochemical composition of sesquiterpenes, diterpenes, triterpenes and other phytochemical(s) obtained from the gum resin of *Boswellia* species.

Another aspect of the disclosure is to provide composition(s) comprising *Boswellia* low polar gum resin extract (BLPRE) in combination with at least one component selected from biologically active ingredient(s), functional ingredient(s), excipient(s), diluents(s), carrier(s) and additive(s) or mixtures thereof.

Another major aspect of the present disclosure is to provide synergistic composition(s) comprising *Boswellia* low polar gum resin extract (BLPRE) in combination with at least one component selected from polar extracts or phytochemicals, or their salts or mixtures, where the polar extracts or phytochemicals are derived from *Boswellia* species.

Another aspect of the present disclosure is to provide synergistic composition(s) comprising *Boswellia* low polar gum resin extract (BLPRE) and at least one component selected from the extract(s), fraction(s), phytochemical(s) and their salts or mixtures thereof derived from *Curcuma* species.

Another aspect of the disclosure is to provide synergistic composition(s) of *Boswellia* low polar gum resin extract (BLPRE) with at least one component selected from but not limited to biologically active ingredient(s), functional ingredient(s) or mixtures thereof.

Another aspect of the disclosure is to provide *Boswellia* low polar gum resin extract (BLPRE) comprising a novel phytochemical composition and its compositions for use in warm blooded animal(s) in need thereof.

Various embodiments disclosed herein relate to a *Boswellia* low polar gum resin extract (BLPRE) comprising a phytochemical composition of sesquiterpenes, diterpenes, triterpenes, and other phytochemicals derived from a gum resin of at least one plant in the genus *Boswellia*. The BLPRE is obtained after selectively removing acidic and volatile compounds from the gum resin. In various embodiments, the *Boswellia* low polar gum resin extract (BLPRE) is derived from a plant selected from the group consisting of *Boswellia serrata, Boswellia carterii, Boswellia papyrifera, Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and *Boswellia socotrana*, and mixtures thereof. In certain embodiments, the plant in the genus *Boswellia* is selected from the group consisting of *Boswellia serrata, Boswellia carterii, Boswellia papyrifera*, and mixtures thereof.

According to certain embodiments, the BLPRE is derived from *Boswellia serrata* gum resin, and comprises at least three compounds selected from guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9), as shown in FIG. 1. The BLPRE is derived from *Boswellia serrata* gum resin after selectively removing acidic and volatile compounds from the gum resin.

Various embodiments of processes for preparation of a composition comprising the BLPRE include the steps of:
a) procuring gum resin of at least one plant of the genus *Boswellia*;
b) preparing an extract solution of the gum resin with a water immiscible organic solvent;
c) evaporating the water immiscible organic solvent from the extract solution to obtain an oily residue; and
d) removing volatile compounds from the oily residue under high vacuum and high temperature to obtain the BLPRE.

Some processes for preparation of a composition comprising the BLPRE include the steps of:
a) procuring gum resin of at least one plant of the genus *Boswellia*;
b) extracting the gum resin with a water immiscible organic solvent, such as 1,2-dichloroethane, hexane, dichloromethane, chloroform, ethyl acetate, n-butanol, methyl iso-butyl ketone (MIBK), or mixtures thereof, to produce a solution of an organic solvent extract;
c) washing the organic solvent extract solution at least once with an aqueous solution of a metal hydroxide salt;
d) subsequent to step (c), washing the organic solvent extract solution with water, brine, or a mixture thereof;
e) evaporating the water immiscible organic solvent from the organic solvent extract solution to obtain an oily residue; and
f) removing volatile compounds from the oily residue under high vacuum and high temperature to obtain the BLPRE.

Other processes for preparation of a composition comprising the BLPRE include the steps of:
a) procuring gum resin of at least one plant of the genus *Boswellia*;
b) extracting the gum resin with an alcoholic solvent or a hydroalcoholic solvent to produce an alcoholic extract solution;
c) evaporating at least a portion of the alcoholic solvent or the hydroalcoholic solvent to produce a concentrated solution;
d) adjusting the pH of the concentrated solution to between about 9 and about 12; and
e) extracting the concentrated solution with the water immiscible organic solvent to produce an extract solution comprising the water immiscible organic solvent;
f) evaporating said water immiscible solvent from the extract solution to obtain an oily residue; and
g) removing volatile compounds from the oily residue under high vacuum and high temperature to obtain the BLPRE.

In certain embodiments, the step of evaporating at least a portion of the alcoholic solvent or the hydroalcoholic solvent comprises evaporating at least 20%, preferably at least 40%, more preferably at least 60% of the alcoholic or hydroalcoholic solvent. In various embodiments, the solvent is a hydroalcoholic solvent, and the step of evaporating at least a portion of the solvent comprises evaporating at least 50%, preferably at least 75%, more preferably substantially all of the alcohol in the hydroalcoholic solvent.

In various embodiments of the processes described above, the term "gum resin of at least one plant of the genus *Boswellia*" may refer to gum resin of at least one plant selected from the group consisting of *Boswellia serrata, Boswellia carterii, Boswellia papyrifera, Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and *Boswellia socotrana*, and mixtures thereof. In some embodiments of these processes, the term "gum resin of at least one plant of the genus *Boswellia*" may refer to gum resin of at least one plant selected from the group consisting of *Boswellia serrata, Boswellia carterii, Boswellia papyrifera*, and mixtures thereof.

According to various processes disclosed herein, a synergistic composition may be prepared by obtaining a boswellic acid-containing extract of at least one plant selected from the group consisting of *Boswellia serrata, Boswellia carterii, Boswellia papyrifera*, and mixtures thereof; combining the BLPRE and the boswellic acid-containing extract in a desired ratio to obtain the synergistic composition; and optionally combining the synergistic composition with at least one component selected from the group consisting of biologically active ingredients, excipients, diluents, carriers and additives.

According to other processes disclosed herein, a synergistic composition may be prepared by obtaining a curcuminoid-containing extract of at least one plant from the genus *Curcuma*; combining the BLPRE and the curcuminoid-containing extract in a desired ratio to obtain the synergistic composition; and optionally combining the synergistic composition with at least one component selected from the group consisting of biologically active ingredients, excipients, diluents, carriers and additives.

Various embodiments disclosed herein relate to compositions comprising the BLPRE and at least one biologically active component selected from the group consisting of at least one boswellic acid or a salt thereof; a boswellic acid-containing extract of at least one plant selected from the group consisting of *Boswellia serrata, Boswellia carterii, Boswellia papyrifera*, and mixtures thereof; at least one curcuminoid or a salt thereof; and a curcuminoid-containing extract of a plant from the genus *Curcuma*. If the biologically active ingredient is a boswellic acid-containing extract, the boswellic acid-containing extract may comprise between about 30% and about 100% total boswellic acids. If the biologically active ingredient is a curcuminoid-containing extract, the curcuminoid-containing extract may comprise between about 20% and 99% of said at least one curcuminoid. The curcuminoid-containing extract may be an extract of a plant selected from the group consisting of *Curcuma longa, Curcuma aromatic*, and mixtures thereof.

In various embodiments, the compositions comprise from about 5% to about 95%, preferably from about 20% to about 80%, more preferably from about 33% to about 67%, by weight of the boswellic acid-containing extract, and from about 5% to about 95%, preferably from about 20% to about 80%, more preferably from about 33% to about 67%, by weight of said BLPRE.

In other embodiments, the compositions comprise from about 5% to about 95%, preferably from about 20% to about 80%, more preferably from about 33% to about 67%, by weight of the curcuminoid-containing extract, and from about 5% to about 95%, preferably from about 20% to about 80%, more preferably from about 33% to about 67%, by weight of said BLPRE.

In additional embodiments, the compositions may additionally comprise at least one component derived from a plant, an animal, a microorganism, or a mixture thereof. The compositions may also comprise one or more ingredients selected from the group consisting of herbal ingredients, antioxidants, vitamins, minerals, amino acids, fatty acids, essential oils, fish oils, enzymes and probiotics.

Various embodiments disclosed herein relate to methods of treating inflammation in a warm blooded animal, by administering the BLPRE to said warm blooded animal. In various embodiments, the BLPRE may be administered alone or in combination with a boswellic acid-containing extract, a curcuminoid-containing extract, or a mixture thereof.

Various embodiments disclosed herein relate to methods of treating a condition associated with at least one biological marker in a warm blooded animal, by administering the BLPRE to said warm blooded animal, said biological marker being selected from the group consisting of 5-lipoxygenase (5-LOX), 5-Lipoxygenase activating protein (FLAP), Macrophage/Adipocyte Fatty acid binding protein (aP2), IFN-γ, IL-4, ICAM, VCAM, MMPs, TNFα, NFκB, IL-1β, and combinations thereof. Again, the BLPRE may be administered alone or in combination with the boswellic acid-containing extract, the curcuminoid-containing extract, or a mixture thereof.

Another aspect of the present disclosure is to provide Boswellia low polar gum resin extract (BLPRE) comprising a novel phytochemical composition alone and its compositions for the prevention, control and treatment of one or more disorder(s) or disease(s) in warm blooded animals, including but not limited to metabolic disorders, diabetes, obesity, metabolic syndrome, excess body weight, inflammation, asthma, Alzheimer's, cognitive disorders, neurological disorders, cartilage degradation, aging, skin disorders, hyper triglyceridemia, hyperlipidemia, hypercholesterolemia, cholesterol disorders, hypertension, high blood pressure, immune disorders, cancer, coronary heart disease, infectious diseases, osteoporosis, osteoarthritis, rheumatoid arthritis, joint pain, joint discomfort and several other conditions associated thereof.

DETAILED DESCRIPTION

Figure 1:
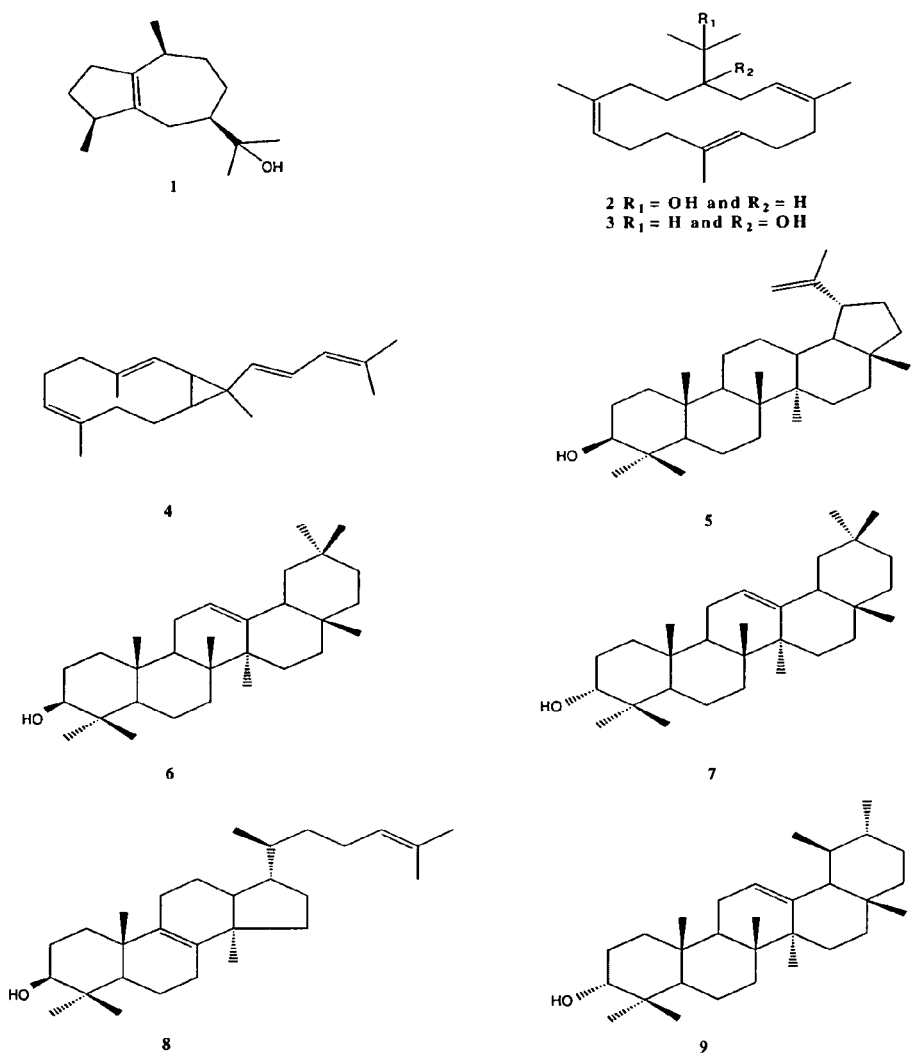
FIG. 1: Figure shows structural formulae 1-9 representing prominent compounds of Boswellia low polar gum resin extract (BLPRE).

Abbreviations and words used in the description:
1. BLPRE (Boswellia low polar gum resin extract obtained from Boswellia species)
2. BsLPRE (Boswellia serrata low polar gum resin extract obtained from Boswellia serrata)
3. BcLPRE (Boswellia carterii low polar gum resin extract obtained from Boswellia carterii)
4. BSE 85% (Boswellia serrata extract standardized to 85% Boswellic acids)
5. BCE 85% (Boswellia carterii extract standardized to 85% Boswellic acids)
6. BSE 65% (Boswellia serrata extract standardized to 65% Boswellic acids)
7. BCE 65% (Boswellia carterii extract standardized to 65% Boswellic acids)
8. CLE 20% (Curcuma longa extract standardized to 20% Curcuminoids)
9. CLE 95% (Curcuma longa extract standardized to 95% Curcuminoids)
10. CAE 20% (Curcuma aromatica extract standardized to 20% Curcuminoids)
11. CAE 95% (Curcuma aromatica extract standardized to 95% Curcuminoids)
12. The terms 'Gum' or 'Gum resin' or 'resin' used in this patent application are meant to be used interchangeably and they all refer to an exudate of Boswellia plant species.
13. The word 'composition' wherever used in the patent application either refers to the novel Boswellia low polar resin extract (BLPRE) as a standalone ingredient or a mixture comprising BLPRE in combination with one or more ingredients such as biologically active ingredient(s), functional ingredient(s), excipient(s), diluents(s), carrier(s) and additive(s) for preparing either general composition(s) or synergistic composition(s).
14. 'Boswellia low polar resin extract' or 'low polar resin extract' wherever used in the patent application refers to the low polar gum resin extract obtained from any of the Boswellia species by any of the processes described.
15. 'Boswellia oil' or 'oily residue' or 'Boswellia oil fraction' wherever used in the present application refers to the total oil fraction/extract (comprising essential oils, volatile oils and Boswellia low polar resin extract) obtained from the gum resin of any of the Boswellia species by any of the processes described.
16. 'Volatile oil' or 'volatile fraction' wherever used in the patent application refers to volatile oils obtained by steam distillation or vacuum distillation of any Boswellia gum resin or Boswellia oil.

17. 'Phytochemical' wherever used in the patent application refers to a pure or semi-pure compound or compounds isolated from plants.
18. The terms 'biologically active ingredient(s)' and 'functional ingredient(s),' wherever used in the patent application, each refer to any pharmaceutically or dietetically acceptable ingredient(s); compound(s), extract(s), fraction(s), phytochemical(s) and their salts or mixtures thereof derived from plants/animals/microorganisms. More particularly, these terms may each refer to any herbal extract(s), dietary supplement(s), antioxidants, vitamins, minerals, amino acids, fatty acids, essential oils, fish oils, enzymes, Glucosamine, Chondroitin and probiotics or mixtures thereof derived from plants/animals/microorganisms.
19. 'Excipients' or 'diluents' or 'carriers' or 'additives' wherever used in the patent application refer to one or more pharmaceutically or dietetically acceptable active or inactive ingredients including but not limited to water, saline, aqueous glucose solution, alcohol (e.g. ethanol), propylene glycol, polyethylene glycol, various animal and vegetable oils, white soft paraffin, paraffin, wax, glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavours and preservatives.

*Boswellia serrata* and *Boswellia carterii* Low Polar Gum Resin Extract:

The gum resin obtained from a *Boswellia* species, which may be, but is not limited to, *Boswellia serrata, Boswellia carterii, Boswellia papyrifera* or mixtures thereof, is a complex mixture comprising essential oil, volatile oils, Boswellic acids, low polar compounds, sugars and polysaccharide fraction. The *Boswellia serrata, Boswellia carterii*, and/or *Boswellia papyrifera* extracts widely available in the international markets are acidic fractions separated from the gum resin which are standardized to contain 65% or 85% total Boswellic acids by titrimetric method of analysis. During the execution of commercial process for regular *Boswellia* extracts derived from *Boswellia serrata/Boswellia carterii/Boswellia papyrifera* (85% total Boswellic acids), the acidic fraction, which contains predominantly triterpene acids including Boswellic acids is separated from the rest of the gum resin components. The sugars and other polymeric materials get separated out into the aqueous phase during the enrichment process for total Boswellic acids. The remaining water immiscible low polar compounds, are separated as a *Boswellia* oil fraction or extract. These low polar compounds are either absent or present at very low concentration in both commercial *Boswellia* extracts standardized to boswellic acids and *Boswellia* extracts selectively enriched in 3-O-acetyl-11-keto-β-Boswellic acid (AKBA).

The *Boswellia* oil fraction or extract constitutes a significant component in *Boswellia* gum resin. However, it has very limited commercial utility and it is mostly discarded as a waste material. Potential utilization of this fraction or extract has been long overdue. The inventors found very unexpectedly that *Boswellia* low polar gum resin extract (BLPRE), a fraction obtained after removing the volatile compounds from the *Boswellia* oil fraction or extract, has several beneficial biological properties. In addition, BLPRE unexpectedly exhibited synergistic activity when combined with other biologically active ingredients.

A representative procedure for obtaining *Boswellia serrata* low polar gum resin extract (BsLPRE) comprises:
a) Procuring the gum resin of *Boswellia serrata*.
b) extraction with an water immiscible organic solvent and the insoluble gum materials were separated by filtration and discarded,
c) washing the organic solvent extract repeatedly with dilute aqueous alkali solution to remove the acidic compounds,
d) washing the organic layer successively with water and brine,
e) evaporating the organic layer under vacuum at 60-70° C. to obtain an oily residue,
f) the volatile components are then removed from the said oily residue under high vacuum and high temperature to obtain a viscous oil, which is referred herein after as *Boswellia serrata* low polar gum resin extract (BsLPRE).

Alternatively, the BsLPRE can also be prepared by a process comprising:
a) preparing the alcohol or hydroalcohol extract of *Boswellia serrata* gum resin,
b) partitioning the alcohol extract between an aqueous alkali solution and a water immiscible organic solvent,
c) separation of the organic solvent layer, followed by evaporating the organic layer under vacuum at 60-70° C. to obtain an oily residue,
d) the volatile components are then removed from the said oily residue under high vacuum and high temperature to obtain a viscous oil, which is referred herein after as *Boswellia serrata* low polar gum resin extract (BsLPRE).

A representative procedure for obtaining *Boswellia carterii* low polar gum resin extract (BcLPRE) comprises:
a) procuring the gum resin of *Boswellia carterii*,
b) extracting the gum resin with an water immiscible organic solvent and the insoluble gum materials were separated by filtration and discarded,
c) washing the organic solvent extract repeatedly with dilute aqueous alkali solution to remove the acidic compounds,
d) washing the organic layer successively with water and brine,
e) evaporating the organic layer under vacuum at 60-70° C. to obtain an oily residue.
f) the volatile components are then removed from the said oily residue under high vacuum and high temperature to obtain a viscous oil, which is referred herein after as *Boswellia carterii* low polar gum resin extract (BcLPRE).

Alternatively, the BcLPRE can also be prepared by process comprising:
a) preparing the alcohol or hydroalcohol extract of *Boswellia carterii* gum resin,
b) partitioning the alcohol extract between an aqueous alkali solution and a water immiscible organic solvent,
c) separation of the organic solvent layer, followed by evaporating the organic layer under vacuum at 60-70° C. to obtain an oily residue,
d) the volatile components are then removed from the said oily residue under high vacuum and high temperature to obtain a viscous oil, which is referred herein after as *Boswellia carterii* low polar gum resin extract (BcLPRE).

The representative processes for obtaining *Boswellia* low polar gum resin extract (BLPRE) from *Boswellia serrata, Boswellia carterii* are described above. However, a similar process or processes can be applied to any of the gum resins obtained from *Boswellia* species for producing the low polar gum resin extract.

In order to understand the chemical composition of BsLPRE, the inventors have carried out extensive separation of BsLPRE using repeated column chromatography and high performance liquid chromatography (HPLC), and isolated several diterpenoid and triterpenoid compounds. The structures of the compounds were rigorously characterized using $^1$H NMR, $^{13}$C NMR, DEPT, HSQC and HMBC, Mass spectral data. The compounds so obtained and identified are guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9) as depicted in FIG. 1. The fraction, *Boswellia serrata* low polar gum resin extract (BsLPRE) was then standardized to three or more of the phytochemical marker compounds selected from 1 to 9. The typical results obtained are summarized in the Table 1 and a typical chromatogram depicting the profile of BsLPRE is presented in FIG. 2. However, the inventors have also found that this composition of BsLPRE or any other *Boswellia* low polar gum resin extract composition (BLPRE) obtained from any other species may vary based on several factors such as *Boswellia* species used, age of the plant, season of collection of gum resin, geographic location and manufacturing process employed.

The foregoing results manifest that BsLPRE is a novel composition comprising unique combination of sesquiterpenoids, diterpenoids and triterpenoids and other phytochemical(s). A compound tentatively identified as diterpene X (4) and compounds guiol (1), nepthenol (2) and Lanosta-8,24-diene-3α-ol (8) are not known to be metabolites of *Boswellia serrata* gum resin. These results suggest that BsLPRE is a novel composition. Surprisingly BsLPRE also exhibited potent biological properties. BsLPRE potently inhibited 5-lipoxygenase enzyme (Table 2). It showed 15.13% inhibition of 5-lipoxygenase at 10 μg/mL concentration.

The identification of the composition of low polar gum resin extract obtained from various *Boswellia* species such as *Boswellia carterii*, *Boswellia papyrifera* is under process. It is contemplated that the low polar gum resin extract of these as well as other *Boswellia* species comprise a composition having some similarity to that of *Boswellia serrata*. However, the low polar gum resin extract of *Boswellia carterii* (BcLPRE) has shown biological activity and synergistic effect very similar to that exhibited by BsLPRE as summarized in the following in vitro and in vivo studies. The experimental studies are discussed in the examples.

Synergistic Composition(s) Comprising *Boswellia* Low Polar Gum Resin Extract (BLPRE):

The inventors have conducted several cell based and enzyme based in vitro studies on a broad array of *Boswellia* extracts, including *Boswellia serrata* low polar gum resin extract (BsLPRE) and *Boswellia carterii* low polar gum resin extract (BcLPRE). Additional studies were performed on *Boswellia* extracts comprising polar compounds such as Boswellic acids, including *Boswellia serrata* extract standardized to 85% Boswellic acids (BSE 85%), *Boswellia serrata* extract standardized to 65% Boswellic acids (BSE 65%), and *Boswellia carterii* extract standardized to 85% Boswellic acids (BCE 85%). Several other herbal extracts were also tested. The individual extracts and different combinations of these extracts were tested for their efficacy to inhibit 5-lipoxygenase enzyme (5-LOX).

It was found very surprisingly that the compositions comprising either BsLPRE or BcLPRE in combination with any one of the following standardized extracts such as BSE 85%, BCE 85%, and BSE 65% at certain ratios showed synergistic inhibition of 5-lipoxygenase enzyme.

The composition-3A (BsLPRE and BSE 85% in 1:2 ratio), showed 27.12% inhibition at 10 μg/mL compared to 15.13% and 21.04% inhibitions shown respectively by BsLPRE and BSE 85% at the same concentrations.

Figure 3:
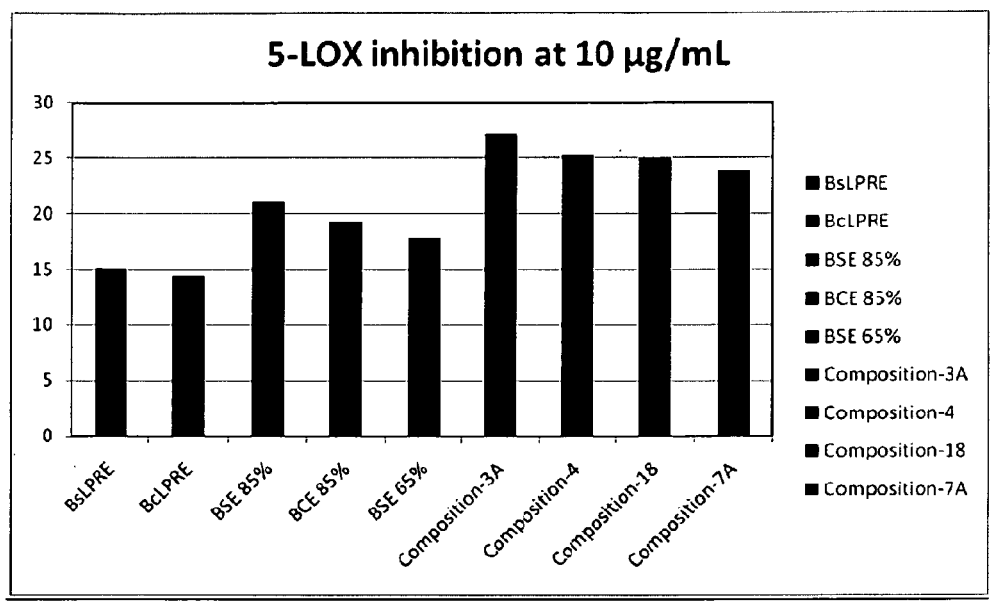
FIG. 3: Figure shows comparative 5-Lipoxygenase inhibitory activity of Boswellia serrata low polar gum resin extract (BsLPRE), Boswellia carterii low polar gum resin extract (BcLPRE), Boswellia serrata extract standardized to 85% total Boswellic acids [BSE 85%], Boswellia carterii extract standardized to 85% total Boswellic acids [BCE 85%], Boswellia serrata extract standardized to 65% total Boswellic acids [BSE 65%], composition-3A, composition-4, composition-18 and composition-7A. The bars represent percentage inhibition of 5-Lipoxygenase enzyme exhibited by BsLPRE, BcLPRE, BSE 85%, BCE 85%, BSE 65%, composition-3A, composition-4, composition-18 and composition-7A at 10 μg/mL concentration.

The comparative 5-lipoxygenase inhibition shown by composition-3A (BsLPRE and BSE 85% in 1:2 ratio), composition-4 (BcLPRE and BCE 85% in 1:2 ratio), composition-18 (BcLPRE and BSE 85% in 1:2 ratio), composition-7A (BsLPRE and BSE 65% in 1:2 ratio), along with those shown by individual ingredients/extracts are presented in FIG. 3.

The synergistic effects shown by composition-3A, composition-4, composition-18, composition-7A in vitro along with few other compositions were then put to test in an in vivo study in Freund's Complete Adjuvant induced arthritis model of Sprague Dawley rats. The anti-inflammatory efficacy of composition-3A, composition-4, composition-18, composition-7A, composition-42 (BsLPRE and CLE 20% in 1:2 ratio), composition-26 (BsLPRE and CLE 95% in 1:2 ratio), composition-51 (BcLPRE and CAE 20% in 1:2 ratio) and composition-35 (BcLPRE and CAE 95% in 1:2 ratio) were evaluated in an in vivo study in Freund's Complete Adjuvant induced arthritis model of Sprague Dawley rats and compared their efficacy with the efficacy shown by the individual ingredients/extracts such as BsLPRE, BcLPRE, BSE 85%, BCE 85%, BSE 65%, CLE 20%, CLE 95%, CAE 20% and CAE 95%. The rats of either sex were randomly selected and divided into nineteen groups containing six animals per group and the treatment groups were supplemented daily with 200 mg/kg body weight (BW) of one of BsLPRE, BcLPRE, BSE 85%, BCE 85%, BSE 65%, CLE 20%, CLE 95%, CAE 20%, CAE 95%, composition-3A, composition-4, composition-18, composition-7A, composition-42, composition-26, composition-51 and composition-35 for 14 days. The positive control group was supplemented daily with Prednisolone at 10 mg/kg body weight. At the 14th day, Freund's Complete Adjuvant (FCA) was injected subcutaneously in the sub-plantar region of the left hind paw of each animal. The experiment was terminated on 28$^{th}$ day. Blood samples were collected from each animal at regular intervals and paw volumes were measured by Plethysmography equipment on the day of FCA injection and after 13 days of FCA inoculation. The difference in volume of paw edema is considered as the inflammatory response. The in vivo anti-inflammatory response of BsLPRE, BcLPRE, BSE 85%, BCE 85%, BSE 65%, CLE 20%, CLE 95%, CAE 20%, CAE 95%, composition-3A, composition-4, composition-18, composition-7A, composition-42, composition-26, composition-51, composition-35 and Prednisolone were estimated by calculating the percentage inhibition of paw edema when compared to the CMC supplemented control.

Figure 4:
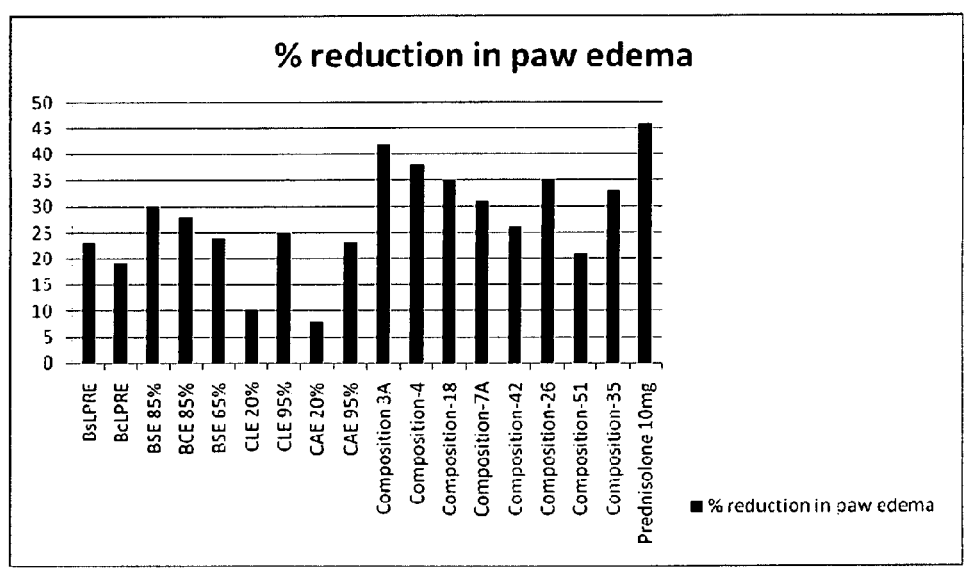
FIG. 4: Figure shows bar diagrammatic representations of percentage inhibition of paw edema volume in Freund's Complete Adjuvant induced Sprague Dawley rats by Boswellia serrata low polar gum resin extract [BsLPRE, 200 mg/kg body weight (BW)], Boswellia carterii low polar gum resin extract (BcLPRE, 200 mg/kg BW), Boswellia serrata extract standardized to 85% total Boswellic acids (BSE 85%, 200 mg/kg BW), Boswellia carterii extract standardized to 85% total Boswellic acids (BCE 85%, 200 mg/kg BW), Boswellia serrata extract standardized to 65% total Boswellic acids (BSE 65%, 200 mg/kg BW), Curcuma longa extract standardized to 20% total curcuminoids (CLE 20%, 200 mg/kg BW), Curcuma longa extract standardized to 95% total curcuminoids (CLE 95%, 200 mg/kg BW), Curcuma aromatica extract standardized to 20% total curcuminoids (CAE 20%, 200 mg/kg BW), Curcuma aromatica extract standardized to 95% total curcuminoids (CAE 95%, 200 mg/kg BW), composition-3A (200 mg/kg BW), composition-4 (200 mg/kg BW), composition-18 (200 mg/kg BW), composition-7A (200 mg/kg BW), composition-42 (200 mg/kg BW), composition-26 (200 mg/kg BW), composition-51 (200 mg/kg BW), composition-35 (200 mg/kg BW) and Prednisolone (10 mg/kg BW).

The treatment groups supplemented with 200 mg/kg body weight of *Boswellia serrata* low polar gum resin extract (BsLPRE) and 200 mg/kg body weight of *Boswellia serrata* extract standardized to 85% total Boswellic acids (BSE 85%) showed 23% and 30% reduction in paw edema respectively. However, the treatment group supplemented with composition-3A (BsLPRE and BSE 85% in 1:2 ratio) at the same dose level showed better reduction and achieved 42% reduction in paw edema volume. The positive control group supplemented with Prednisolone exhibited 46% inhibition at 10 mg/kg dose level. Similarly, the other inventive compositions composition-4, composition-18, composition-7A, composition-42, composition-26, composition-51 and composition-35 also exhibited synergistic effects as summarized in FIG. 4 and Table 3 confirming the observed in vitro results.

Therefore, the foregoing data shows that the compositions comprising either BsLPRE or BcLPRE in combination with a standardized extract of *Boswellia* species such as, BSE 85%, BCE 85% and BSE 65% or a standardized extract of *Curcuma* species such as CLE 20%, CLE 95%, CAE 20% and CAE 95% in the ratio of 1:2 are more potent as anti-inflammatory agents compared to the efficacy shown by the individual components at the same dose levels, manifesting an unexpected synergistic association between these extracts.

*Boswellia serrata* and *Boswellia carterii* low polar gum resin extracts (BsLPRE and BcLPRE respectively) obtained after removing the volatile compounds have been used to demonstrate the present disclosure. However, *Boswellia* oil fraction obtained from any of the *Boswellia* species or volatile fraction obtained from any of the *Boswellia* species or fractions obtained after partially removing the volatiles from *Boswellia* oil or mixtures thereof can also be used for making the compositions and synergistic composition(s) of the disclosure, and for obtaining the intended therapeutic/health benefits in warm blooded animal(s).

The *Boswellia* low polar gum resin extracts, used for demonstrating the present disclosure, have been obtained from *Boswellia serrata* and *Boswellia carterii* and the names BsLPRE and BcLPRE respectively have been chosen arbitrarily for them. However, the inventors have found that low polar gum resin extract (BLPRE) with similar chemical and biological properties can also be derived from other *Boswellia* species using similar processes as shown in Example-1 and Example-2.

Commercially available *Boswellia serrata* extract and *Boswellia carterii* extract standardized to 85% Boswellic acids have been used for making the composition(s) to demonstrate the present disclosure. However, any *Boswellia* extract(s) or fraction(s) or *Boswellia* extracts standardized to at least one or more Boswellic acids or their salts; extract(s)/fraction(s) standardized to 50-100% total Boswellic acids by titrimetric method of analysis or extract(s)/fraction(s) standardized to 30%-100% total Boswellic acids by HPLC method of analysis or extract(s)/fraction(s) having 3-O-acetyl-11-keto-β-Boswellic acid (AKBA) concentration in the range of 0.1-99% can also be used to make the compositions described in the present disclosure.

The BLPRE produced from *Boswellia serrata* or *Boswellia carterii* when combined with an array of *Boswellia* or *Curcuma* extracts showed synergistic activity. However, BLPRE produced from other *Boswellia* species is also useful in preparing the synergistic composition(s).

DESCRIPTION OF VARIOUS EMBODIMENTS

In an important aspect, the disclosure provides a *Boswellia* low polar gum resin extract (BLPRE) comprising novel phytochemical composition of sesquiterpenes, diterpenes, triterpenes, and other phytochemical(s) obtained from *Boswellia* gum resin.

In another aspect, the disclosure provides *Boswellia* low polar gum resin extract (BLPRE) where in the gum resin can be obtained/originated from any of the *Boswellia* species including but not limited to *Boswellia serrata, Boswellia carterii* and *Boswellia papyrifera* or mixtures thereof.

In another aspect, the disclosure provides a *Boswellia* low polar gum resin extract from *Boswellia serrata* gum resin, wherein the said extract comprises phytochemical marker compounds selected from but not limited to guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9).

In another aspect, the disclosure provides a process for producing *Boswellia* low polar resin extract (BLPRE) comprising the following steps:
a) extraction of the gum resin of *Boswellia* species with a water immiscible organic solvent and filtering the extract carefully to remove the insoluble resin material.
b) washing the organic solvent extract repeatedly with an aqueous alkali solution such as aqueous potassium hydroxide
c) washing the organic layer obtained after the alkali wash, with water and brine,
d) evaporating the said organic layer under vacuum and high temperature to obtain the oily residue (*Boswellia* oil),
e) removing the volatile compounds from the said oily residue under high vacuum and high temperature to obtain *Boswellia* low polar resin extract (BLPRE).

The water immiscible organic solvent used for extraction may be, but is not limited to 1,2-dichloroethane, hexane, dichloromethane, chloroform, ethyl acetate, n-butanol, methyl iso-butyl ketone (MIBK), hydrocarbon solvents, or combinations thereof.

The alkali solution used for washing the organic solvent extract can be selected from Group-I or Group-II metal hydroxides, including but not limited to Sodium hydroxide, Potassium hydroxide, Calcium hydroxide and Magnesium hydroxide or mixtures thereof.

In another aspect, an alternative process for producing BLPRE comprise:
a) preparing the alcohol or hydroalcohol extract of *Boswellia* gum resin,
b) partitioning the alcohol extract between an aqueous alkali solution and a water immiscible organic solvent,
c) separation of the organic solvent layer, followed by evaporation of the solvent to obtain oily residue (*Boswellia* oil),
d) removal of volatile compounds from the said oily residue under high temperature and high vacuum to obtain *Boswellia* low polar gum resin extract (BLPRE).

In another aspect, a further alternative process for producing *Boswellia* low polar gum resin extract (BLPRE) comprise,
a) extracting the gum resin of *Boswellia* species with alcohol or hydro alcohol,
b) evaporating the organic solvent to an optimum level of total solids and then
c) adjusting the pH to the alkaline side, preferably pH 9-12,
d) repeatedly extracting the solution with an organic solvent,
e) evaporating the organic solvent under vacuum and high temperature to obtain the oily residue (*Boswellia* oil),
f) evaporating the volatiles from the said oily residue under high vacuum and high temperature to obtain BLPRE.

The alcohol used for extraction can be selected from the group comprising but not limited to methanol, ethanol and propanol or their suitable combination thereof.

In various embodiments, the disclosure provides the synergistic composition(s) comprising *Boswellia* low polar gum resin extract (BLPRE) and at least one component selected from the extract(s) or fraction(s) or phytochemical(s) or their salt(s) or mixtures thereof derived from *Boswellia* species. In some embodiments, the disclosure provides the synergistic composition(s) comprising *Boswellia* low polar gum resin extract (BLPRE) and at least one component selected from boswellic acid containing extracts derived from *Boswellia* species.

In other aspects, the disclosure provides synergistic composition(s) comprising BLPRE and at least one component selected from the extract(s) or fraction(s) or phytochemical(s) or their salt(s) or mixtures thereof derived from *Curcuma* species. In some aspects, the disclosure provides synergistic composition(s) comprising *Boswellia* low polar gum resin extract (BLPRE); and at least one component selected from curcuminoid-containing extracts derived from *Curcuma* species.

In some aspects, the disclosure provides synergistic composition(s) comprising *Boswellia* low polar gum resin extract (BLPRE); at least one component selected from the boswellic acid containing extracts derived from *Boswellia* species; and at least one component selected from curcuminoid-containing extracts derived from *Curcuma* species.

In various aspects, the disclosure provides a *Boswellia* low polar gum resin extract, which is low polar, obtained after selectively removing the acidic and volatile compounds.

In another aspect, the disclosure provides the use of one or more components selected from *Boswellia* oil fraction obtained from any of the *Boswellia* species or volatile fraction obtained from any of the *Boswellia* species or fractions obtained after partially removing the volatiles from *Boswellia* oil in place of BLPRE for preparing composition(s) described in the patent application.

In another aspect, the disclosure provides the *Boswellia* extract(s) or fraction(s) or pure phytochemicals or their salts or their mixtures thereof preferably obtained from *Boswellia serrata* or *Boswellia carterii* or *Boswellia papyrifera* for preparing the compositions with BLPRE.

In further aspects, the disclosure provides the synergistic composition(s) comprising BLPRE with one or more selected from the *Boswellia* extract(s), fraction(s) and extracts/fractions enriched in total Boswellic acids in the range of 50-100%, by the titrimetric method of analysis or 30-100%, by HPLC method of analysis.

In yet another aspect, the disclosure provides synergistic composition(s) comprising BLPRE and one or more component(s) selected from the extract(s), fraction(s) and phytochemical(s) comprising Boswellic acids either individually or in combination selected from α-Boswellic acid, β-Boswellic acid, 3-O-acetyl-α-Boswellic acid, 3-O-acetyl-β-Boswellic acid, 3-O-acetyl-11-keto-α-Boswellic acid, 11-keto-β-Boswellic acid and 3-O-acetyl-11-keto-β-Boswellic acid and their salts.

In another aspect, the disclosure provides synergistic composition(s) comprising BLPRE and one or more component(s) selected from the extract(s), fraction(s) and phytochemical(s) comprising Boswellic acids either individually or in combination selected from α-Boswellic acid in the range of 0.1-20%, β-Boswellic acid in the range of 0.1-50%, 3-O-acetyl-α-Boswellic acid in the range of 0.1-20%, 3-O-acetyl-β-Boswellic acid in the range of 0.1-99%, 3-O-acetyl-11-keto-α-Boswellic acid 0.1-20%, 11-keto-β-Boswellic acid in the range of 0.1-99% and 3-O-acetyl-11-keto-β-Boswellic acid in the range of 0.1-99% and their salts.

In another aspect the disclosure provides, compositions comprising BLPRE and one or more selected from extract(s), fraction(s), phytochemical(s) and their salts derived from the *Curcuma* species.

In another aspect the disclosure provides, composition(s) comprising BLPRE and at least one or more component(s) selected from the extract(s), fraction(s), phytochemical(s), and their salts derived from *Curcuma* species, extracts/fractions enriched/standardized to Curcuminoids either individually or in combination in the range of 20-99% by HPLC method of analysis.

In another aspect the disclosure provides, compositions comprising BLPRE and one or more *Curcuma* derived components selected from curcumin, demethoxycurcumin, bisdemethoxycurcumin, monodemethylcurcumin, bisdemethylcurcumin, tetrahydro-curcumin, tetrahydrodemethoxycurcumin, tetrahydro bisdemethoxycurcumin, arturmerone and their salts obtained naturally or by synthesis or by semi-synthesis.

In another aspect, the disclosure provides process for producing synergistic composition(s) comprising the steps:
(a) extraction of the gum resin of *Boswellia serrata* or *Boswellia carterii* or *Boswellia papyrifera* with a water immiscible organic solvent,
(b) filtering the extract carefully to remove the insoluble resin material,
(c) washing the organic solvent extract repeatedly with an aqueous alkali solution such as aqueous potassium hydroxide,
(d) washing the said alkali washed organic solvent extract with successively water and brine,
(e) evaporating the organic layer under vacuum and high temperature to obtain an oily residue,
(f) removing the volatile compounds from the said oily residue under high vacuum and high temperature to obtain the *Boswellia* low polar resin extract (BLPRE).
(g) separately, obtaining a *Boswellia* derived component selected from the extract(s) or fraction(s) or pure compound(s), extracts/fractions selectively enriched in one or more boswellic acid(s) or mixtures thereof,
(h) combining the said BLPRE and at least one *Boswellia* derived component(s) in a desired ratio to obtain synergistic composition(s),
(i) optionally mixing the said composition(s) with one or more biologically active ingredients, functional ingredients, excipients, diluents, carriers and additives.

In another aspect, the disclosure provides process for producing synergistic composition(s) comprising the steps:
(a) extraction of the gum resin of *Boswellia serrata* or *Boswellia carterii* or *Boswellia papyrifera* with a water immiscible organic solvent,
(b) filtering the extract carefully to remove the insoluble resin material,
(c) washing the organic solvent extract repeatedly with an aqueous alkali solution such as aqueous potassium hydroxide,
(d) washing the said alkali washed organic solvent extract successively with water and brine,
(e) evaporating the organic layer under vacuum and high temperature to obtain an oily residue,
(f) removing the volatile compounds from the said oily residue under high vacuum and high temperature to obtain the *Boswellia* low polar resin extract (BLPRE).
(g) separately, obtaining a *Curcuma* derived component(s) selected from the extract(s) or fraction(s), extracts/fractions enriched with one or more Curcuminoids, pure Curcuminoid compounds or mixtures thereof,
(h) combining the said BLPRE and at least one *Curcuma* derived component(s) in a desired ratio to obtain synergistic composition(s),
(i) optionally mixing the said composition(s) with one or more biologically active ingredients, functional ingredients, excipients, diluents, carriers and additives.

In another aspect, the disclosure provides synergistic composition(s) comprising preferably 5%-95% by weight of *Boswellia* low polar resin extract (BLPRE) and preferably 95%-5% by weight of at least one *Boswellia* derived component selected from extract(s), fraction(s), extracts and fractions standardized to one or more boswellic acids, pure boswellic acid(s), phytochemical(s) and their salts or mixtures thereof.

In another aspect, the disclosure provides synergistic composition(s) comprising more preferably 20%-80% by weight of *Boswellia* low polar resin extract (BLPRE) and more preferably 80%-20% by weight of at least one *Boswellia* derived component selected from extract(s), fraction(s), extracts and fractions standardized to one or more boswellic acids, pure boswellic acid(s), phytochemical(s) and their salts or mixtures thereof.

In another aspect, the disclosure provides *Boswellia* low polar gum resin extract (BLPRE), *Boswellia* oil, Boswellic acid(s), extract(s), fraction(s), extracts and fractions enriched in one or more boswellic acids, phytochemical(s) and their salts derived from *Boswellia* species, wherein the *Boswellia* species include but not limited to *Boswellia serrata, Boswellia carterii, Boswellia papyrifera, Boswellia sacra, Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae* and *Boswellia socotrana*.

In another aspect of the disclosure, the composition of BsLPRE or BLPRE varies based on several factors such as *Boswellia* species used, age of the plant, season of collection of gum resin, geographic location and manufacturing process employed.

In another aspect, the disclosure provides the synergistic compositions comprising preferably 5%-95% by weight of *Boswellia* low polar resin extract (BLPRE) and preferably 95%-5% by the weight of at least one *Curcuma* derived component selected from extract(s), fraction(s), extracts/fractions standardized to one or more curcuminoids, pure curcuminoid(s), phytochemical(s) and their salts or mixtures thereof.

In another aspect, the disclosure provides synergistic composition(s) comprising more preferably 20%-80% by weight of BLPRE and more preferably 80%-20% by weight of at least one *Curcuma* derived component selected from extract(s), fraction(s), extracts and fractions standardized to one or more curcuminoids, pure curcuminoid(s), phytochemical(s) and their salts or mixtures thereof.

In another aspect, the disclosure provides extract(s), fraction(s), extract(s)/fraction(s) selectively enriched in curcuminoids, Curcuminoids, phytochemical(s) and their salts derived from *Curcuma* species, wherein the *Curcuma* species include but not limited to *Curcuma longa, Curcuma aromatica, Curcuma zedoaria, Curcuma domestica, Curcuma aeruginosa, Curcuma albicoma, Curcuma albiflora, Curcuma alismatifolia, Curcuma angustifolia, Curcuma elata, Curcuma ferruginea, Curcuma flaviflora, Curcuma yunnanensis,* and *Curcuma zedoaroides*.

In another major aspect, the disclosure provides composition(s) comprising *Boswellia* low polar resin extract (BLPRE) and one or more component(s) selected from biologically active ingredient(s), functional ingredient(s), excipient(s), diluent(s), carrier(s) and additive(s).

In another aspect, the Biologically active ingredients used for preparing the composition(s) include but not limited to pharmaceutically or dietetically acceptable active ingredient(s), anti-inflammatory agents, anti-obese agents, anti-diabetic agents, anti-arthritic agents, anti-asthmatic agents, anti-cancer agents, compound(s), extract(s), fraction(s), phytochemical(s) and their salts or mixtures thereof derived from plants, animals or microorganisms.

In another aspect, the functional ingredient(s) used for preparing composition(s) include but not limited to herbal ingredient(s), dietary supplements, antioxidants, vitamins, minerals, amino acids, fatty acids, essential oils, fish oils, enzymes, Glucosamine, chondroitin and probiotics.

In another aspect, the herbal ingredient(s) used for preparing composition(s) include extracts/fractions/phytochemicals derived from plants selected from but not limited to *Withania somnifera, Garcinia mangostana, Garcinia cambogia, Piper nigrum, Piper betle, Piper longum, Bacopa monniera, Centella asiatica, Amorphophallus campanulatus, Amorphophallus konjac, Emblica officinalis, Holoptelea integrifolia, Ocimum tenuiflorum, Annona squamosa* and *Sphaeranthus indicus*.

In another aspect, the disclosure provides composition(s) for the prevention, control or treatment of one or more diseases or disorders in warm blooded animal(s).

In another embodiment of the disclosure excipients/diluents/additives/sweetening agents/flavoring agents/wetting agents/absorbents/solution retarding agents include but not limited to distilled water, saline, aqueous glucose solution, alcohol (e.g. ethanol), propylene glycol, polyethylene glycol, various animal and vegetable oils, white soft paraffin, paraffin, wax, glucose, fructose, sucrose, maltose, saccharin, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, cetyl alcohol, glyceryl monostearate, kaolin, betonite clay pigments, peppermint, methyl salicylate, orange flavor, vanilla flavor and preservatives alone or in a suitable combination thereof.

In another aspect, the disclosure provides for administration of *Boswellia* low polar gum resin extract (BLPRE) alone or its composition(s) in comminuted form or in unmodified form in a suitable dosage form selected from but not limited to an infusion solution, injection solution, tablet, capsule, cream, gel, granules, precipitate, extract, liquid, syrup, shots, exudates, ointment, enema, medicinal pack, topical patches, controlled release tablets, controlled release capsules or food supplement.

In another aspect, the disclosure provides for formulation of *Boswellia* low polar gum resin extract (BLPRE) alone or its composition(s) into suitable forms including but not limited to oral agents such as tablets, capsules, soft capsules, hard capsules, pills, granules, powders, emulsions, suspensions, syrups and pellets; as parenteral agents such as injection solution, drops and suppositories; and as transdermal agents such as patches, topical creams and gel and food ingredients or beverages.

In another aspect the disclosure provides use of the composition(s) for the prevention, control and treatment of disorders or diseases in warm-blooded animals in need thereof.

In another aspect, the disclosure provides a method of using a therapeutically effective amount of *Boswellia* low polar gum resin extract (BLPRE) alone or its composition(s) for the prevention, control and treatment of diseases or disorders selected from but not limited to inflammation, metabolic disorders, inflammatory disorders, asthma, atherosclerosis, endothelial dysfunction, osteoarthritis, rheumatoid arthritis, allergic rhinitis, dermatitis, psoriasis, cystic fibrosis, inflammatory bowel diseases, multiple sclerosis, diabetes, memory loss, neurological disorders, cartilage degradation, aging, skin disorders, disorders in cholesterol levels (LDL, VLDL and HDL), hyper triglyceridemia, hyperlipidemia, hypercholesterolemia, hypertension, high blood pressure, immune disorders, coronary heart disease, vasculitis, ulcerative colitis, gastrointestinal allergies, nephritis, conjunctivitis, chronic obstructive pulmonary disease, occupational asthma, eczema, bronchitis, hay fever, hives, adult respiratory distress syndrome, allergic disorders and for conditions like wheezing, dyspnea, non productive cough, chest tightness, neck muscle tightness, rapid heart rate, chest pain, infectious diseases, osteoporosis, joint pain, joint discomfort, cognitive disorders and several other conditions associated thereof in warm blooded animals in need thereof.

In another aspect, administration of a therapeutically effective amount of *Boswellia* low polar gum resin extract (BL-PRE) alone or its composition(s) for the prevention, control and treatment of disease conditions related to or associated with inflammation, which include but not limited to asthma, occupational asthma, eczema, bronchitis, hay fever, hives, rheumatoid arthritis, juvenile rheumatoid arthritis, psoriatic arthritis, osteoarthritis, refractory rheumatoid arthritis, chronic non-rheumatoid arthritis, osteoporosis, coronary heart disease, atherosclerosis, endothelial dysfunction, multiple sclerosis, vasculitis, nephritis, uveitis, glomerulonephritis, systemic lupus erythematosis, post-angioplasty restenosis, ulcerative colitis, conjunctivitis, dermatitis, psoriasis, cystic fibrosis, adult respiratory distress syndrome, IBS (inflammatory bowel syndrome), IBD (inflammatory bowel disease), chronic obstructive pulmonary disease, adult respiratory distress syndrome, allergic rhinitis, gastrointestinal allergies, allergic disorders and for conditions like wheezing, dyspnea, non productive cough, chest tightness, neck muscle tightness, rapid heart rate, joint pain, and delayed-type hypersensitivity in warm blooded animals in need thereof.

In another aspect, the disclosure provides *Boswellia* low polar gum resin extract (BLPRE) alone or its composition(s) for the amelioration of one or more biological markers, which include but not limited to 5-lipoxygenase (5-LOX), 5-Lipoxygenase activating protein (FLAP), Macrophage/Adipocyte Fatty acid binding protein (aP2), IFN-γ, IL-4, ICAM, VCAM, MMPs, TNFα, NFκB and IL-1β by composition(s) in warm blooded animals in need thereof.

In another aspect, the disclosure provides a method of use of *Boswellia* low polar gum resin extract (BLPRE) alone or its composition(s) for the amelioration of one or more biological markers, which include but not limited to 5-lipoxygenase (5-LOX), 5-Lipoxygenase activating protein (FLAP), Macrophage/Adipocyte Fatty acid binding protein (aP2), IFN-γ, IL-4, ICAM, VCAM, MMPs, TNFα, NFκB and IL-1β by composition(s) in warm blooded animals in need thereof.

EXAMPLES

Example 1

Preparation of *Boswellia serrata* Low Polar Gum Resin Extract (BsLPRE)

The *Boswellia serrata* gum resin (100 g) was dispersed in 600 mL of methyl isobutyl ketone (MIBK) solvent and stirred at room temperature for 60 min. The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under vacuum at 60-70° C. and the volatile components are then removed from the oily residue under high vacuum at 75-85° C. to obtain BsLPRE as viscous oil (12 g).

Alternatively, the gum resin (250 g) collected from *Boswellia serrata* was extracted with methanol (300 mL×3) and the combined methanol extract was concentrated. The residue (50 g) was dissolved in ethyl acetate (400 mL) and extracted thrice with 1N KOH (3×100 mL). The organic layer was washed with water (2×200 mL) and brine (200 mL) and evaporated to obtain oily residue (*Boswellia* oil). The volatile compounds were evaporated from the oil under high vacuum at 75-85° C. to obtain 22 g of BsLPRE.

Figure 2:
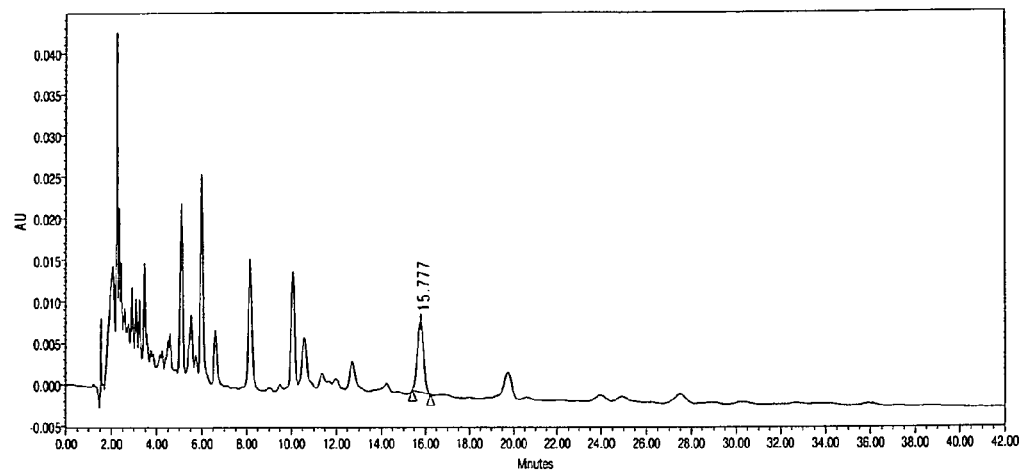
FIG. 2: Figure shows the HPLC chromatogram depicting the phytochemical profile of Boswellia low polar gum resin extract (BLPRE).
Figure 2:
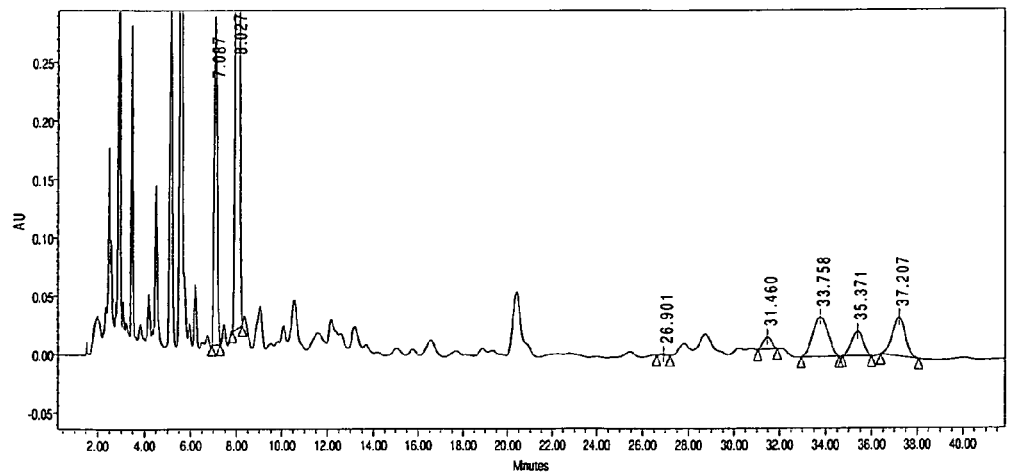

The BsLPRE was subjected to column chromatography over normal silica gel using solvents of increasing polarity starting from hexane to hexane/ethyl acetate mixtures to ethyl acetate. The identical fractions were combined based on TLC and the combined fractions were subjected individually to repeated column over silica gel using mixtures of hexane/ethyl acetate or hexane/acetone as eluants to obtain pure compounds. Some of the impure fractions were further subjected to preparative HPLC using a reversed phase C18 silica column to obtain pure compounds. The structures of individual compounds were established by analyzing the $^1$H NMR, $^{13}$C NMR, DEPT, HSQC and HMBC and mass spectral data and then comparing the data with that of known compounds. Nine of the prominent compounds are identified as guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9) as depicted in FIG. 1. The pure compounds were then utilized to standardize the *Boswellia serrata* low polar extract (BLPRE) using HPLC method. The novel composition of BLPRE, evaluated based on analytical HPLC method, along with the retention times ($R_t$) is summarized in Table 1. The HPLC chromatogram for BLPRE is depicted in FIG. 2.

Guaiol (1):

$^1$H NMR (CDCl$_3$, 400 MHz): δ 2.57-2.53 (1H, m), 2.46-2.39 (1H, m), 2.33-2.30 (1H, m), 2.28-2.22 (1H, m), 2.09-1.89 (2H, m), 1.84-1.75 (2H, m), 1.67-1.52 (2H, m), 1.48-1.28 (3H, m), 1.18 (6H, s), 1.03 (3H, d, J=7.2 Hz), 0.99 (3H, d, J=6.8 Hz); $^{13}$C NMR (CDCl$_3$, 100 MHz): δ 140.98, 140.02, 73.80, 49.84, 45.10, 35.27, 33.83, 33.32, 31.28, 29.20, 27.35, 27.11, 26.27, 19.61, 19.26.

Nephthenol (2):

$^1$H NMR (CDCl$_3$, 400 MHz): δ 5.12 (1H, t, J=7.0 Hz), 5.00 (1H, t, J=6.4 Hz), 4.94 (1H, t, J=6.4 Hz), 2.20 (2H, m), 2.14 (2H, m), 2.12 (1H, m), 2.07 (2H, m), 2.03 (2H, m), 2.00 (2H, m), 1.90 (1H, dd, J=14.0, 7.0 Hz), 1.65 (1H, m), 1.57 (6H, s), 1.56 (3H, s), 1.34 (1H, m), 1.28 (1H, m), 1.20 (6H, s); $^{13}$C NMR (CDCl$_3$, 100 MHz): δ 134.09, 133.39, 133.08, 125.98, 125.80, 125.02, 73.94, 48.59, 39.42, 38.88, 37.81, 31.93, 29.69, 28.54, 28.34, 27.70, 27.57, 27.35, 24.73, 24.07, 15.61, 15.58, 15.33. Mass 290 C$_{20}$H$_{34}$O Diterpene X (4)

$^1$H NMR (CDCl$_3$), 400 MHz: δ 6.17 (1H, dd, J=10.8, 15.2 Hz), 5.78 (1H, d, J=7.2 Hz), 5.28 (1H, d, J=15.2 Hz), 4.87 (1H, m), 4.41 (1H, d, J=11.2 Hz), 2.44 (1H, m), 2.26 (1H, dt, J=3.2, 11.6 Hz), 2.11 (1H, m), 2.20 (2H, m), 1.75 (3H, s), 1.75 (6H, s), 1.72 (1H, d) 1.66 (3H, s), 1.60 (2H, m), 1.49 (3H, d, J=0.8 Hz) 1.34 (1H, m), 1.19 (3H, s), 0.94 (1H, m); $^{13}$C NMR(CDCl$_3$), 100 MHz: δ 12.05, 16.55, 18.22, 20.80, 25.84, 26.00, 26.45, 28.77, 29.66, 30.58, 37.08, 41.15, 121.48, 125.08, 125.12, 129.10, 132.05, 140.50, 141.89.

Lanosta-8,24-diene-3α-ol (8):

$^1$H NMR (CDCl$_3$, 400 MHz): δ 5.10 (1H, t, J=6.8 Hz), 3.43 (1H, t, J=2.4 Hz), 2.12-1.85 (8H, m), 1.71 (2H, m), 1.65 (3H, s), 1.59 (3H, s), 1.65-1.29 (10H, m), 1.26 (3H, s), 1.213-1.16 (1H, m), 0.97 (3H, s), 0.96 (3H, s), 0.92 (3H, d, J=6.4 Hz), 0.87 (6H, s), 0.77 (3H, s); $^{13}$C NMR (CDCl$_3$, 100 MHz): δ 134.44, 133.42, 130.87, 125.35, 76.02, 50.24, 50.09, 44.92, 44.20, 37.73, 37.27, 36.48, 36.36, 30.92, 29.88, 29.72, 28.09, 27.31, 25.94, 25.70, 25.01, 24.43, 22.30, 21.46, 20.00, 18.90, 18.75, 17.63, 15.60.

TABLE 1

Composition of *Boswellia serrata* low polar gum resin extract (BsLPRE)

| S. No | Test substance | $R_t$ in min | Percentage |
|---|---|---|---|
| 1 | Guiol (1) | 4.5 | 0.96 |
| 2 | Nephthenol (2) | 7.087 | 2.01 |
| 3 | Serratol (3) | 8.027 | 13.32 |
| 4 | Diterpene X (4) | 15.777 | 0.12 |
| 5 | Lupeol (5) | 26.901 | 0.06 |
| 6 | Olean-12-ene-3β-ol (6) | 31.460 | 1.29 |
| 7 | Olean-12-ene-3α-ol (7) | 33.718 | 5.36 |
| 8 | Lanosta-8,24-diene-3α-ol (8) | 35.371 | 1.34 |
| 9 | Urs-12-ene-3α-ol (9) | 37.207 | 4.55 |

Example 2

Preparation of *Boswellia carterii* Low Polar Gum Resin Extract (BcLPRE)

The *Boswellia carterii* gum resin (100 g) was dispersed in 600 mL of methyl isobutyl ketone (MIBK) solvent and stirred at room temperature for 60 min. The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under reduced pressure at 60-70° C. and the volatile components are then removed from the oily residue under high vacuum at 75-85° C. to obtain BcLPRE as a viscous oil (9.5 g).

Alternatively, the gum resin (250 g) collected from *Boswellia carterii* was extracted with methanol (300 mL×3) and the combined methanol extract was concentrated. The residue (50 g) was dissolved in ethyl acetate (400 mL) and extracted thrice with 1N KOH (3×100 mL). The organic layer was washed with water (2×200 mL) and brine (200 mL) and evaporated to obtain oily residue. The volatile compounds were evaporated from the oil under high vacuum at 75-85° C. to obtain 17.75 g of BcLPRE.

Example 3

*Boswellia serrata* Extract Standardized to 50-100% Total Boswellic Acids by Titrimetric Method or to 30-100% Total Boswellic Acids by HPLC Method of Analysis

*Boswellia serrata* extracts standardized to 85% or 65% total Boswellic acids by titrimetric method of analysis are commercially available. Alternately, these extracts can be prepared using a known procedure. For example, by extracting the gum resin of *Boswellia serrata* using a water immiscible organic solvent and then selectively extracting the acidic compounds from the organic solvent extract using aqueous alkali solution through phase separation. Finally acidification of the alkali solution to precipitate the Boswellic acids followed by filtration and vacuum drying of the resultant solid to yield *Boswellia serrata* extract standardized to 85% Boswellic acids (BSE85%). *Boswellia serrata* extracts standardized to a selected concentration of total Boswellic acids in the range of 50-100% by titrimetric method of analysis or 30-100% by HPLC method of analysis can be obtained by purification of the *Boswellia serrata* gum resin or *Boswellia serrata* extracts or by dilution of higher grade material.

Example 4

*Boswellia carterii* Extract Standardized to 50-100% Total Boswellic Acids (Titrimetric Method)

*Boswellia carterii* extracts standardized to 85% or 65% total Boswellic acids by titrimetric method of analysis can be prepared using a procedure described in Example 3 for *Boswellia serrata*. For example, by extracting the gum resin of *Boswellia carterii* using a water immiscible solvent and then selectively extracting the acidic compounds from the organic solvent extract using aqueous alkali solution through phase separation. Finally acidification of the alkali solution to precipitate the Boswellic acids followed by filtration and vacuum drying of the solid to yield *Boswellia carterii* extract standardized to 85% total boswellic acids (BCE85%). *Boswellia carterii* extracts standardized to a selected concentration of total Boswellic acids in the range of 50-100% by titrimetric method of analysis or 30-100% by HPLC method of analysis can be obtained by purification of the *Boswellia carterii* gum resin or *Boswellia carterii* extracts or by dilution of higher grade material.

Example 5

Preparation of Composition-1

Composition-1 was prepared by mixing unit doses of the following components; one part of *Boswellia serrata* low polar gum resin extract (BsLPRE) (1 g) and one part of *Boswellia serrata* extract standardized to 85% total Boswellic acids (BSE 85%) (1 g).

Example 6

Preparation of Composition-2

Composition-2 was prepared by mixing unit doses of the following components; one part of *Boswellia carterii* low polar gum resin extract (BcLPRE) (1 g) and one part of *Boswellia carterii* extract standardized to 85% total Boswellic acids (BCE 85%) (1 g).

Example 7

Preparation of Composition-3A

Composition-3A was prepared by mixing unit doses of the following components; one part of *Boswellia serrata* low polar gum resin extract (BsLPRE) (1 g) and two parts of *Boswellia serrata* extract standardized to 85% total Boswellic acids (BSE 85%) (2 g).

Preparation of Composition-3B

Composition-3B was prepared by mixing unit doses of the following components; one part of *Boswellia serrata* low polar gum resin extract (BsLPRE) (1 g) and two parts of *Boswellia carterii* extract standardized to 85% total Boswellic acids (BCE 85%) (2 g).

Example 8

Preparation of Composition-4

Composition-4 was prepared by mixing unit doses of the following components; one part of *Boswellia carterii* low polar gum resin extract (BcLPRE) (1 g) and two parts of *Boswellia carterii* extract standardized to 85% total Boswellic acids (BCE 85%) (2 g).

Example 9

Preparation of Composition-5

Composition-5 was prepared by mixing unit doses of the following components; two parts of *Boswellia serrata* low polar gum resin extract (BsLPRE) (2 g) and one part of *Boswellia serrata* extract standardized to 85% Boswellic acids (BSE 85%) (1 g).

Example 10

Preparation of Composition-6

Composition-6 was prepared by mixing unit doses of the following components; two parts of *Boswellia carterii* low polar gum resin extract (BcLPRE) (2 g) and one part of *Boswellia carterii* extract standardized to 85% Boswellic acids (BCE 85%) (1 g).

Example 11

Preparation of Composition-7A

Composition-7A was prepared by mixing unit doses of the following components; one part of *Boswellia serrata* low polar gum resin extract (BsLPRE) (1 g) and two parts of *Boswellia serrata* extract standardized to 65% Boswellic acids (BSE 65%) (2 g).

Preparation of Composition-7B

Composition-7B was prepared by mixing unit doses of the following components; one part of *Boswellia serrata* low polar gum resin extract (BsLPRE) (1 g) and two parts of *Boswellia carterii* extract standardized to 65% Boswellic acids (BCE 65%) (2 g).

Example 12

Preparation of Composition-8

Composition-8 was prepared by mixing unit doses of the following components; one part of *Boswellia carterii* low polar gum resin extract (BcLPRE) (1 g) and two parts of *Boswellia carterii* extract standardized to 65% Boswellic acids (BCE 65%) (2 g).

Example 13

Preparation of Composition-9

Composition-9 was prepared by mixing unit doses of the following components; one part of *Boswellia serrata* low polar gum resin extract (BsLPRE) (1 g) and one part of *Boswellia serrata* extract standardized to 65% Boswellic acids (BSE 65%) (1 g).

Example 14

Preparation of Composition-10

Composition-10 was prepared by mixing unit doses of the following components; one part of *Boswellia carterii* low polar gum resin extract (BcLPRE) (1 g) and one part of *Boswellia carterii* extract standardized to 65% Boswellic acids (BCE 65%) (1 g).

Example 15

Composition-11

Composition-11 was prepared by mixing unit doses of the following components; two parts of *Boswellia serrata* low polar gum resin extract (BsLPRE) (2 g), two parts of *Boswellia serrata* extract standardized to 85% Boswellic acids (BSE 85%) (2 g) and one part of white dextrin (1 g).

Example 16

Composition-12

Composition-12 was prepared by mixing unit doses of the following components; two parts of *Boswellia carterii* low polar gum resin extract (BcLPRE) (2 g), two parts of *Boswellia carterii* extract standardized to 85% Boswellic acids (BCE 85%) (2 g) and one part of white dextrin (1 g).

Example 17

Composition-13

Composition-13 was prepared by mixing unit doses of the following components; one part of *Boswellia serrata* low polar gum resin extract (BsLPRE) (2 g), two parts of *Boswellia serrata* extract enriched with 95% of 3-O-acetyl-11-keto-β-Boswellic acid (4 g).

Example 18

Composition-14

Composition-14 was prepared by mixing unit doses of the following components; one part of *Boswellia carterii* low polar gum resin extract (BcLPRE) (2 g), two parts of *Boswellia carterii* extract enriched with 95% of 3-O-acetyl-11-keto-β-Boswellic acid (4 g).

Example 19

Composition-15

Composition-15 was prepared by mixing unit doses of the following components; one part of *Boswellia serrata* low polar gum resin extract (BsLPRE) (2 g), two parts of *Boswellia serrata* extract enriched with 40% of 3-O-acetyl-β-Boswellic acid (4 g).

Example 20

Composition-16

Composition-16 was prepared by mixing unit doses of the following components; one part of *Boswellia carterii* low polar gum resin extract (BcLPRE) (2 g), two parts of *Boswellia carterii* extract enriched with 40% of 3-O-acetyl-β-Boswellic acid (4 g).

Example 21

Preparation of Composition-17

Composition-17 was prepared by mixing unit doses of the following components; one part of *Boswellia carterii* low polar gum resin extract (BcLPRE) (1 g) and one part of *Boswellia serrata* extract standardized to 85% total Boswellic acids (BSE 85%) (1 g).

Example 22

Preparation of Composition-18

Composition-18 was prepared by mixing unit doses of the following components; one part of *Boswellia carterii* low polar gum resin extract (BcLPRE) (1 g) and two parts of *Boswellia serrata* extract standardized to 85% total Boswellic acids (BSE 85%) (2 g).

Example 23

Preparation of Composition-19

Composition-19 was prepared by mixing unit doses of the following components; one part of *Boswellia carterii* low polar gum resin extract (BcLPRE) (1 g), two parts of *Boswellia serrata* extract standardized to 85% total Boswellic acids (BSE 85%) (2 g) and one part of white dextrin (1 g).

Example 24

Preparation of Composition-20

Composition-20 was prepared by mixing unit doses of the following components; two parts of *Boswellia carterii* low polar gum resin extract (BcLPRE) (2 g) and one part of *Boswellia serrata* extract standardized to 85% Boswellic acids (BSE 85%) (1 g).

Example 25

Preparation of Composition-21

Composition-21 was prepared by mixing unit doses of the following components; one part of *Boswellia serrata* low polar gum resin extract (BsLPRE) (1 g) and one part of *Boswellia carterii* extract standardized to 85% total Boswellic acids (BCE 85%) (1 g).

Example 26

Preparation of Composition-22A

Composition-22A was prepared by mixing unit doses of the following components; one part of *Boswellia serrata* low polar gum resin extract (BsLPRE) (1 g) and two parts of *Boswellia carterii* extract standardized to 85% total Boswellic acids (BCE 85%) (2 g).

Preparation of Composition-22B

Composition-22B was prepared by mixing unit doses of the following components; two parts of *Boswellia serrata* low polar gum resin extract (BsLPRE) (2 g) and one part of *Boswellia carterii* extract standardized to 85% Boswellic acids (BCE 85%) (1 g).

Example 27

Preparation of Composition-23

Composition-23 was prepared by mixing unit doses of the following components; one part of *Boswellia serrata* low polar gum resin extract (BsLPRE) (1 g), two parts of *Boswellia carterii* extract standardized to 85% total Boswellic acids (BCE 85%) (2 g) and one part of white dextrin (1 g).

Example 28

Preparation of *Curcuma longa* Extract 20-99% Curcuminoids (CLE 20-99%) or *Curcuma aromatica* Extract 20-99% Curcuminoids (CAE 20-99%)

The *Curcuma* extract standardized to 95% curcuminoids is an enriched product obtained from *Curcuma* species and it comprises curcumin, demethoxycurcumin and bis-demethoxycurcumin. These and low assay *curcuma* extracts can be procured from the commercially available extracts or can be produced using one or more of the following procedures. Extraction of *Curcuma longa* rhizome with methanol followed by evaporation of the solvent and washing the residue with hexane gives 20-25% total Curcuminoids by HPLC. Precipitation of this 20-25% total Curcuminoids product in n-butanol/hexane mixture gives a residue, which on vacuum drying gives 90-95% total Curcuminoids by HPLC. Optionally, extraction of *Curcuma longa* rhizome with acetone or ethyl acetate followed by evaporation of the solvent gives *Curcuma longa* extract comprising 50-60% total Curcuminoids. Alternately the low grade extracts can be purified to required concentration of total Curcuminoids using, precipitations, washings, chromatography techniques, resin purifications or combinations thereof. Similar processes or techniques can also be applied to other *Curcuma* species including but not limited to *Curcuma aromatica, Curcuma zedoaria* and *Curcuma amada* to obtain required concentration of total Curcuminoids.

Example 29

Preparation of Composition-24

Composition-24 was prepared by mixing unit doses of the following components; one part of *Boswellia serrata* low polar gum resin extract (BsLPRE) (1 g) and one part of *Curcuma longa* extract standardized to 95% total Curcuminoids (CLE 95%) (1 g).

Example 30

Preparation of Composition-25

Composition-25 was prepared by mixing unit doses of the following components; one part of *Boswellia carterii* low polar gum resin extract (BcLPRE) (1 g) and one part of *Curcuma longa* extract standardized to 95% total Curcuminoids (CLE 95%) (1 g).

Example 31

Preparation of Composition-26

Composition-26 was prepared by mixing unit doses of the following components; one part of *Boswellia serrata* low polar gum resin extract (BsLPRE) (1 g) and two parts of *Curcuma longa* extract standardized to 95% total Curcuminoids (CLE 95%) (2 g).

Example 32

Preparation of Composition-27

Composition-27 was prepared by mixing unit doses of the following components; one part of *Boswellia carterii* low polar gum resin extract (BcLPRE) (1 g) and two parts of *Curcuma longa* extract standardized to 95% total Curcuminoids (CLE 95%) (2 g).

Example 33

Preparation of Composition-28

Composition-28 was prepared by mixing unit doses of the following components; one part of *Boswellia serrata* low polar gum resin extract (BsLPRE) (1 g), two parts of *Curcuma longa* extract standardized to 95% total Curcuminoids (CLE 95%) (2 g) and one part of white dextrin (1 g).

Example 34

Preparation of Composition-29

Composition-29 was prepared by mixing unit doses of the following components; one part of *Boswellia carterii* low polar gum resin extract (BcLPRE) (1 g), two parts of *Curcuma longa* extract standardized to 95% total Curcuminoids (CLE 95%) (2 g) and one part of white dextrin (1 g).

Example 35

Preparation of Composition-30

Composition-30 was prepared by mixing unit doses of the following components; two parts of *Boswellia serrata* low polar gum resin extract (BsLPRE) (2 g) and one part of *Curcuma longa* extract standardized to 95% total Curcuminoids (CLE 95%) (1 g).

Example 36

Preparation of Composition-31

Composition-31 was prepared by mixing unit doses of the following components; two parts of *Boswellia carterii* low polar gum resin extract (BcLPRE) (2 g) and one part of *Curcuma longa* extract standardized to 95% total Curcuminoids (CLE 95%) (1 g).

Example 37

Preparation of Composition-32

Composition-32 was prepared by mixing unit doses of the following components; one part of *Boswellia serrata* low polar gum resin extract (BsLPRE) (1 g) and one part of *Curcuma aromatica* extract standardized to 95% total Curcuminoids (CAE 95%) (1 g).

Example 38

Preparation of Composition-33

Composition-33 was prepared by mixing unit doses of the following components; one part of *Boswellia carterii* low polar gum resin extract (BcLPRE) (1 g) and one part of *Curcuma aromatica* extract standardized to 95% total Curcuminoids (CAE 95%) (1 g).

Example 39

Preparation of Composition-34

Composition-34 was prepared by mixing unit doses of the following components; one part of *Boswellia serrata* low polar gum resin extract (BsLPRE) (1 g) and two parts of *Curcuma aromatica* extract standardized to 95% total Curcuminoids (CAE 95%) (2 g).

Example 40

Preparation of Composition-35

Composition-35 was prepared by mixing unit doses of the following components; one part of *Boswellia carterii* low polar gum resin extract (BcLPRE) (1 g) and two parts of *Curcuma aromatica* extract standardized to 95% total Curcuminoids (CAE 95%) (2 g).

Example 41

Preparation of Composition-36

Composition-36 was prepared by mixing unit doses of the following components; one part of *Boswellia serrata* low polar gum resin extract (BsLPRE) (1 g), two parts of *Curcuma aromatica* extract standardized to 95% total Curcuminoids (CAE 95%) (2 g) and one part of white dextrin (1 g).

Example 42

Preparation of Composition-37

Composition-37 was prepared by mixing unit doses of the following components; one part of *Boswellia carterii* low polar gum resin extract (BcLPRE) (1 g), two parts of *Curcuma aromatica* extract standardized to 95% total Curcuminoids (CAE 95%) (2 g) and one part of white dextrin (1 g).

Example 43

Preparation of Composition-38

Composition-38 was prepared by mixing unit doses of the following components; two parts of *Boswellia serrata* low polar gum resin extract (BsLPRE) (2 g) and one part of *Curcuma aromatica* extract standardized to 95% total Curcuminoids (CAE 95%) (1 g).

Example 44

Preparation of Composition-39

Composition-39 was prepared by mixing unit doses of the following components; two parts of *Boswellia carterii* low polar gum resin extract (BcLPRE) (2 g) and one part of *Curcuma aromatica* extract standardized to 95% total Curcuminoids (CAE 95%) (1 g).

Example 45

Preparation of Composition-40

Composition-40 was prepared by mixing unit doses of the following components; one part of *Boswellia serrata* low polar gum resin extract (BsLPRE) (1 g) and one part of *Curcuma longa* extract standardized to 20% total Curcuminoids (CLE 20%) (1 g).

Example 46

Preparation of Composition-41

Composition-41 was prepared by mixing unit doses of the following components; one part of *Boswellia carterii* low polar gum resin extract (BcLPRE) (1 g) and one part of *Curcuma longa* extract standardized to 20% total Curcuminoids (CLE 20%) (1 g).

Example 47

Preparation of Composition-42

Composition-42 was prepared by mixing unit doses of the following components; one part of *Boswellia serrata* low polar gum resin extract (BsLPRE) (1 g) and two parts of *Curcuma longa* extract standardized to 20% total Curcuminoids (CLE 20%) (2 g).

Example 48

Preparation of Composition-43

Composition-43 was prepared by mixing unit doses of the following components; one part of *Boswellia carterii* low polar gum resin extract (BcLPRE) (1 g) and two parts of *Curcuma longa* extract standardized to 20% total Curcuminoids (CLE 20%) (2 g).

Example 49

Preparation of Composition-44

Composition-44 was prepared by mixing unit doses of the following components; one part of *Boswellia serrata* low polar gum resin extract (BsLPRE) (1 g); two parts of *Curcuma longa* extract standardized to 20% total Curcuminoids (CLE 20%) (2 g) and one part of white dextrin (1 g).

Example 50

Preparation of Composition-45

Composition-45 was prepared by mixing unit doses of the following components; one part of *Boswellia carterii* low polar gum resin extract (BcLPRE) (1 g), two parts of *Curcuma longa* extract standardized to 20% total Curcuminoids (CLE 20%) (2 g) and one part of white dextrin (1 g).

Example 51

Preparation of Composition-46

Composition-46 was prepared by mixing unit doses of the following components; two parts of *Boswellia serrata* low polar gum resin extract (BsLPRE) (2 g) and one part of *Curcuma longa* extract standardized to 20% total Curcuminoids (CLE 20%) (1 g).

Example 52

Preparation of Composition-47

Composition-47 was prepared by mixing unit doses of the following components; two parts of *Boswellia carterii* low polar gum resin extract (BcLPRE) (2 g) and one part of *Curcuma longa* extract standardized to 20% total Curcuminoids (CLE 20%) (1 g).

Example 53

Preparation of Composition-48

Composition-48 was prepared by mixing unit doses of the following components; one part of *Boswellia serrata* low polar gum resin extract (BsLPRE) (1 g) and one part of *Curcuma aromatica* extract standardized to 20% total Curcuminoids (CAE 20%) (1 g).

Example 54

Preparation of Composition-49

Composition-49 was prepared by mixing unit doses of the following components; one part of *Boswellia carterii* low polar gum resin extract (BcLPRE) (1 g) and one part of *Curcuma aromatica* extract standardized to 20% total Curcuminoids (CAE 20%) (1 g).

Example 55

Preparation of Composition-50

Composition-50 was prepared by mixing unit doses of the following components; one part of *Boswellia serrata* low polar gum resin extract (BsLPRE) (1 g) and two parts of *Curcuma aromatica* extract standardized to 20% total Curcuminoids (CAE 20%) (2 g).

Example 56

Preparation of Composition-51

Composition-51 was prepared by mixing unit doses of the following components; one part of *Boswellia carterii* low polar gum resin extract (BcLPRE) (1 g) and two parts of *Curcuma aromatica* extract standardized to 20% total Curcuminoids (CAE 20%) (2 g).

Example 57

Preparation of Composition-52

Composition-52 was prepared by mixing unit doses of the following components; one part of *Boswellia serrata* low polar gum resin extract (BsLPRE) (1 g), two parts of *Curcuma aromatica* extract standardized to 20% total Curcuminoids (CAE 20%) (2 g) and one part of white dextrin (1 g).

Example 58

Preparation of Composition-53

Composition-53 was prepared by mixing unit doses of the following components; one part of *Boswellia carterii* low polar gum resin extract (BcLPRE) (1 g), two parts of *Curcuma aromatica* extract standardized to 20% total Curcuminoids (CAE 20%) (2 g) and one part of white dextrin (1 g).

Example 59

Preparation of Composition-54

Composition-54 was prepared by mixing unit doses of the following components; two parts of *Boswellia serrata* low polar gum resin extract (BsLPRE) (2 g) and one part of *Curcuma aromatica* extract standardized to 20% total Curcuminoids (CAE 20%) (1 g).

Example 60

Preparation of Composition-55

Composition-55 was prepared by mixing unit doses of the following components; two parts of *Boswellia carterii* low polar gum resin extract (BcLPRE) (2 g) and one part of *Curcuma aromatica* extract standardized to 20% total Curcuminoids (CAE 20%) (1 g).

Example 61

Preparation of Composition-56

Composition-56 was prepared by mixing unit doses of the following components; one part of *Boswellia serrata* low polar gum resin extract (BsLPRE) (1 g) and two parts of *Withania somnifera* methanol extract (2 g).

Example 62

Preparation of Composition-57

Composition-57 was prepared by mixing unit doses of the following components; one part of *Boswellia serrata* low polar gum resin extract (BsLPRE) (1 g) and two parts of *Garcinia mangostana* methanol extract (2 g).

Example 63

Preparation of Composition-58

Composition-58 was prepared by mixing unit doses of the following components; one part of *Boswellia serrata* low polar gum resin extract (BsLPRE) (1 g) and two parts of *Annona squamosa* ethanol extract (2 g).

Example 64

Preparation of Composition-59

Composition-59 was prepared by mixing unit doses of the following components; one part of *Boswellia serrata* low polar gum resin extract (BsLPRE) (1 g) and two parts of *Sphaeranthus indicus* ethyl acetate extract (2 g).

Example 65

Preparation of Composition-60

Composition-60 was prepared by mixing unit doses of the following components; one part of *Boswellia serrata* low polar gum resin extract (BsLPRE) (1 g) and two parts of *Bacopa monniera* 90% methanol/water extract (2 g).

Example 66

Evaluation of 5-Lipoxygenase Inhibitory Activity of BsLPRE, BcLPRE, BSE 85%, BCE 85%, BSE 65%, Composition-3A, Composition-4, Composition-18 and Composition-7A 5-Lipoxygenase enzyme inhibitory activity was measured using the method of Schewe et al. (Adv Enzymol, Vol 58, 191-272, 1986), modified by Reddanna et. al., (Methods of Enzymology, Vol 187, 268-277, 1990). The assay mixture contained 80 µM linoleic acid and sufficient amount of potato 5-lipoxygenase in 50 mM phosphate buffer (pH 6.3). The reaction was initiated by the addition of enzyme buffer mix to linoleic acid and the enzyme activity was monitored as the increase in absorbance at 234 nm. The reaction was monitored for 120 sec and the inhibitory potential of the test substances, BsLPRE, BcLPRE, BSE 85%, BCE 85%, BSE 65%, composition-3A, composition-4, composition-18 and composition-7A was measured by incubating various concentrations of test substances two minutes before the addition of linoleic acid. All assays were performed three times. Percentage inhibition was calculated by comparing slope of the curve obtained for test substances with that of the control. The percentage inhibitions of BsLPRE, BcLPRE, BSE 85%, BCE 85%, BSE 65%, composition-3A, composition-4, composition-18 and composition-7A are summarized in Table 2 and depicted in the FIG. 3.

TABLE 2

5-Lipoxygenase inhibitory activity

| S. No | Test substance | 5-LOX inhibition at 10 µg/ml |
|---|---|---|
| 1 | BsLPRE | 15.13 |
| 2 | BcLPRE | 14.36 |
| 3 | BSE 85% | 21.04 |
| 4 | BCE 85% | 19.26 |
| 5 | BSE 65% | 17.68 |
| 6 | Composition-3A | 27.12 |
| 7 | Composition-4 | 25.23 |
| 8 | Composition-18 | 24.95 |
| 9 | Composition-7A | 23.83 |

Example 67

The In Vivo Anti-Inflammatory Activity of *Boswellia* Low Polar Gum Resin Extract (BsLPRE and BcLPRE), a Few *Boswellia* Extracts, *Curcuma* Extracts and their Compositions The anti-inflammatory efficacy of BsLPRE, BcLPRE, BSE 85%, BCE 85%, BSE 65%, CLE 20%, CLE 95%, CAE 20%, CAE 95%, composition-3A, composition-4, composition-18, composition-7A, composition-42, composition-26, composition-51 and composition-35 were evaluated in an in vivo study in Freund's Complete Adjuvant induced arthritis model of Sprague Dawley rats. Prednisolone was used as a positive control. The rats of either sex were randomly selected and divided into nineteen groups containing six animals per group. The treatment group rats were supplemented daily with 200 mg/kg body weight of one of BsLPRE, BcLPRE, BSE 85%, BCE 85%, BSE 65%, CLE 20%, CLE 95%, CAE 20%, CAE 95%, composition-3A, composition-4, composition-18, composition-7A, composition-42, composition-26, composition-51 and composition-35 for 14 days. The positive control group was supplemented daily with Prednisolone at 10 mg/kg body weight. All supplements were diluted in 10 mL of 1% CMC for administration. The animals of control group received same volume of 1% CMC. At the 14th day, Freund's Complete Adjuvant (FCA) was injected subcutaneously in the sub-plantar region of the left hind paw of each animal. The experiment was terminated on $28^{th}$ day. Blood samples were collected from each animal at regular intervals and paw volumes were measured by Plethysmography equipment on the day of FCA injection and after 13 days of FCA inoculation. The difference in volume of paw edema is considered as the inflammatory response. The in vivo anti-inflammatory response of BsLPRE, BcLPRE, BSE 85%, BCE 85%, BSE 65%, CLE 20%, CLE 95%, CAE 20%, CAE 95%, composition-3A, composition-4, composition-18, composition-7A, composition-42, composition-26, composition-51, composition-35 and Prednisolone were estimated by calculating the percentage inhibition of paw edema when compared to the CMC supplemented control.

The treatment groups supplemented with 200 mg/kg body weight of *Boswellia serrata* low polar gum resin extract (BsLPRE) and 200 mg/kg body weight of *Boswellia serrata* extract standardized to 85% total Boswellic acids (BSE 85%) showed 23% and 30% reduction in paw edema respectively. However, the treatment group supplemented with composition-3A at the same dose level showed better reduction and achieved 42% reduction in paw edema volume. The positive control group supplemented with Prednisolone exhibited 46% inhibition at 10 mg/kg dose level. Similarly, the other inventive compositions composition-4, composition-18, composition-7A, composition-42, composition-26, composition-51 and composition-35 also exhibited synergistic effects as summarized in FIG. 4 and Table 3 confirming the observed in vitro results.

TABLE 3

Reduction in Paw volume activity

| S. No | Test substance | Reduction in Paw edema | Concentration mg/kg body weight |
|---|---|---|---|
| 1 | BsLPRE | 23 | 200 |
| 2 | BcLPRE | 19 | 200 |
| 3 | BSE 85% | 30 | 200 |
| 4 | BCE 85% | 28 | 200 |
| 5 | BSE 65% | 24 | 200 |
| 6 | CLE 20% | 10 | 200 |
| 7 | CLE 95% | 25 | 200 |
| 8 | CAE 20% | 8 | 200 |
| 9 | CAE 95% | 23 | 200 |
| 10 | Composition-3A | 42 | 200 |
| 11 | Composition-4 | 38 | 200 |
| 12 | Composition-18 | 35 | 200 |
| 13 | Composition-7A | 31 | 200 |
| 14 | Composition-42 | 26 | 200 |
| 15 | Composition-26 | 35 | 200 |
| 16 | Composition-51 | 21 | 200 |
| 17 | Composition-35 | 33 | 200 |
| 18 | Prednisolone | 46 | 10 |

It will be appreciated by those of ordinary skilled in the art that changes could be made to the embodiments described above without departing from the broad inventive concept thereof. It is understood, therefore, that this invention is not limited to the particular embodiments or examples disclosed, but is intended to cover modifications within the embodiments and scope of the present invention.

What is claimed is:

1. A *Boswellia* gum resin extract derived from a gum resin of at least one plant in the genus *Boswellia*,
   wherein said *Boswellia* gum resin extract is obtained by:
   a) extracting the *Boswellia* gum resin with a solvent to obtain a *Boswellia* extract;
   b) partitioning the *Boswellia* extract between an aqueous alkali solution and a water-immiscible organic solvent;
   c) evaporating the water-immiscible organic solvent to obtain a water immiscible organic solvent extract of *Boswellia*; and
   d) at least partially evaporating volatile components from the water-immiscible organic solvent extract of *Boswellia* under high vacuum at an elevated temperature.

2. The *Boswellia* gum resin extract as claimed in claim 1, wherein said at least one plant in the genus *Boswellia* is selected from the group consisting of *Boswellia serrata*, *Boswellia carterii*, *Boswellia papyrifera*, *Boswellia ameero*, *Boswellia bullata*, *Boswellia dalzielii*, *Boswellia dioscorides*, *Boswellia elongata*, *Boswellia frereana*, *Boswellia nana*, *Boswellia neglecta*, *Boswellia ogadensis*, *Boswellia pirottae*, *Boswellia popoviana*, *Boswellia rivae*, *Boswellia sacra* and *Boswellia socotrana*, and mixtures thereof.

3. The *Boswellia* gum resin extract as claimed in claim 1, wherein said at least one plant in the genus *Boswellia* is selected from the group consisting of *Boswellia serrata*, *Boswellia carterii*, *Boswellia papyrifera*, and mixtures thereof.

4. The *Boswellia* gum resin extract as claimed in claim 1, wherein said at least one plant in the genus *Boswellia* is selected from the group consisting of *Boswellia serrata*, and
   wherein said *Boswellia* gum resin extract comprises at least three compounds selected from guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9).

5. A composition comprising the *Boswellia* gum resin extract according to claim 1, said composition further comprising at least one component selected from the group consisting of distilled water, saline solution, aqueous glucose solution, alcohol, propylene glycol, polyethylene glycol, glycerin, animal oils, vegetable oils, white soft paraffin, paraffin, wax, glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives.

6. A composition comprising the *Boswellia* gum resin extract as claimed in claim 1, said composition further comprising at least one component selected from the group consisting of a biologically active ingredient, an excipient, a diluent, a carrier, an additive, and mixtures thereof.

7. The composition as claimed in claim 6, wherein said biologically active ingredient comprises at least one component derived from a plant, an animal, a microorganism, or a mixture thereof.

8. The composition as claimed in claim 6, wherein said biologically active ingredient comprises one or more ingredients selected from the group consisting of herbal ingredients, antioxidants, vitamins, minerals, amino acids, fatty acids, essential oils, fish oils, enzymes and probiotics.

9. The composition as claimed in claim 6, wherein the composition comprises said biologically active ingredient, said biologically active ingredient comprising at least one component selected from the group consisting of:
   i. at least one boswellic acid or a salt thereof;
   ii. a boswellic acid-containing extract of at least one plant selected from the group consisting of *Boswellia serrata*, *Boswellia carterii*, *Boswellia papyrifera*, and mixtures thereof;
   iii. at least one curcuminoid or a salt thereof; and
   iv. a curcuminoid-containing extract of a plant from the genus *Curcuma*.

10. The composition as claimed in claim 9, wherein said biologically active ingredient is said boswellic acid-containing extract, said boswellic acid-containing extract comprising between about 30% and about 100% total boswellic acids.

11. The composition as claimed in claim 10, wherein said composition comprises from about 5% to about 95% by weight of said boswellic acid-containing extract, and from about 5% to about 95% by weight of said *Boswellia* gum resin extract.

12. The composition as claimed in claim 10, wherein said composition comprises from about 20% to about 80% by weight of said boswellic acid-containing extract, and from about 20% to about 80% by weight of said *Boswellia* gum resin extract.

13. The composition as claimed in claim 10, wherein said composition comprises from about 33% to about 67% by weight of said boswellic acid-containing extract, and from about 33% to about 67% by weight of said *Boswellia* gum resin extract.

14. The composition as claimed in claim 9, wherein said biologically active ingredient is said curcuminoid-containing extract, said curcuminoid-containing extract comprising between about 20% and 99% of said at least one curcuminoid.

15. The composition as claimed in claim 14, wherein said curcuminoid-containing extract is an extract of a plant selected from the group consisting of *Curcuma longa, Curcuma aromatica*, and mixtures thereof.

16. The composition as claimed in claim 15, wherein said composition comprises from about 5% to about 95% by weight of said curcuminoid-containing extract, and from about 5% to about 95% by weight of said *Boswellia* gum resin extract.

17. The composition as claimed in claim 15, wherein said composition comprises from about 20% to about 80% by weight of said curcuminoid-containing extract, and from about 20% to about 80% by weight of said *Boswellia* gum resin extract.

18. The composition as claimed in claim 15, wherein said composition comprises from about 33% to about 67% by weight of said curcuminoid-containing extract, and from about 33% to about 67% by weight of said *Boswellia* gum resin extract.

19. A method of treating inflammation in a warm blooded animal, comprising administering the *Boswellia* gum resin extract as claimed in claim 1 to said warm blooded animal, said *Boswellia* gum resin extract optionally being administered in combination with at least one component selected from the group consisting of:
   i. at least one boswellic acid or a salt thereof;
   ii. a boswellic acid-containing extract of at least one plant selected from the group consisting of *Boswellia serrata, Boswellia carterii, Boswellia papyrifera*, and mixtures thereof;
   iii. at least one curcuminoid or a salt thereof; and
   iv. a curcuminoid-containing extract of a plant from the genus *Curcuma*.

20. The method as claimed in claim 19, wherein said administering comprises administering the *Boswellia* gum resin extract to said warm blooded animal by an oral, dermal, intravenous, subcutaneous, intra-peritoneal, rectal or intramuscular route.

21. A method of treating a condition associated with at least one biological marker in a warm blooded animal, comprising administering the *Boswellia* gum resin extract as claimed in claim 1 to said warm blooded animal in need thereof, said *Boswellia* gum resin extract optionally being administered in combination with at least one component selected from the group consisting of:
   i. at least one boswellic acid or a salt thereof;
   ii. a boswellic acid-containing extract of at least one plant selected from the group consisting of *Boswellia serrata, Boswellia carterii, Boswellia papyrifera*, and mixtures thereof;
   iii. at least one curcuminoid or a salt thereof; and
   iv. a curcuminoid-containing extract of a plant from the genus *Curcuma*,
   said biological marker being selected from the group consisting of 5-lipoxygenase (5-LOX), 5-Lipoxygenase activating protein (FLAP), Macrophage/Adipocyte Fatty acid binding protein (aP2), IFN-γ, IL-4, ICAM, VCAM, MMPs, TNFα, NFκB, IL-1β, and combinations thereof.

22. A process for preparation of a composition comprising *Boswellia* gum resin extract, wherein the process comprises:
   a) extracting the *Boswellia* gum resin with a solvent to obtain a *Boswellia* extract;
   b) partitioning the *Boswellia* extract between an aqueous alkali solution and a water-immiscible organic solvent;
   c) evaporating the water-immiscible organic solvent to obtain a water-immiscible organic solvent extract of *Boswellia*; and
   d) at least partially evaporating volatile components from the water-immiscible organic solvent extract of *Boswellia* under high vacuum at an elevated temperature.

23. The process as claimed in claim 22, wherein the water-immiscible organic solvent is selected from the group consisting of 1,2-dichloroethane, hexane, dichloromethane, chloroform, ethyl acetate, n-butanol, methyl iso-butyl ketone (MIBK), and mixtures thereof.

24. The process as claimed in claim 22, wherein the alkali solution is an aqueous solution of a metal hydroxide selected from the group consisting of Group I metal hydroxide, Group II metal hydroxide, and mixtures thereof.

25. The process according to claim 22, further comprising:
   (e) obtaining a boswellic acid-containing extract of at least one plant selected from the group consisting of *Boswellia serrata, Boswellia carterii, Boswellia papyrifera*, and mixtures thereof;
   (f) combining the *Boswellia* gum resin extract and the boswellic acid-containing extract in a desired ratio to obtain a synergistic composition; and
   (g) optionally combining the synergistic composition with at least one component selected from the group consisting of biologically active ingredients, excipients, diluents, carriers and additives.

26. The process according to claim 22, further comprising:
   (e) obtaining a curcuminoid-containing extract of at least one plant from the genus *Curcuma*;
   (f) combining the *Boswellia* gum resin extract and the curcuminoid-containing extract in a desired ratio to obtain a synergistic composition; and
   (g) optionally combining the synergistic composition with at least one component selected from the group consisting of biologically active ingredients, excipients, diluents, carriers and additives.

27. The process for preparation of a composition comprising *Boswellia* gum resin extract according to claim 22, wherein:
   said extracting comprises extracting the *Boswellia* gum resin with an alcoholic solvent or a hydroalcoholic solvent to produce an alcoholic extract; and
   said partitioning comprises partitioning the alcoholic extract between said aqueous alkali solution and said water-immiscible organic solvent.

28. The process for preparation of a composition comprising *Boswellia* gum resin extract according to claim 22, wherein:

said extracting comprises extracting the *Boswellia* gum resin with a water-immiscible organic solvent to produce an water-immiscible organic solvent extract solution; and said partitioning comprises extracting the water-immiscible organic solvent extract solution with said aqueous alkali solution.

* * * * *